US011052162B2

(12) United States Patent
Annapragada et al.

(10) Patent No.: US 11,052,162 B2
(45) Date of Patent: Jul. 6, 2021

(54) LIPOSOMAL GADOLINIUM (GD) CONTRAST AGENT "NMRX" FOR T1-MRI

(71) Applicant: TEXAS CHILDREN'S HOSPITAL, Houston, TX (US)

(72) Inventors: Ananth Annapragada, Manvel, TX (US); Anil Shetty, Sugarland, TX (US); Ketankumar B Ghaghada, Sugarland, TX (US); Eric Tanifum, Houston, TX (US)

(73) Assignee: TEXAS CHILDREN'S HOSPITAL, Houston, TX (US)

( * ) Notice: Subject to any disclaimer, the term of this patent is extended or adjusted under 35 U.S.C. 154(b) by 179 days.

(21) Appl. No.: 16/333,832

(22) PCT Filed: Sep. 15, 2017

(86) PCT No.: PCT/IB2017/055611
§ 371 (c)(1),
(2) Date: Mar. 15, 2019

(87) PCT Pub. No.: WO2018/051289
PCT Pub. Date: Mar. 22, 2018

(65) Prior Publication Data
US 2019/0255196 A1 Aug. 22, 2019

Related U.S. Application Data

(60) Provisional application No. 62/395,836, filed on Sep. 16, 2016.

(51) Int. Cl.
A61K 49/18 (2006.01)
A61K 49/10 (2006.01)
C07F 5/00 (2006.01)

(52) U.S. Cl.
CPC .......... *A61K 49/1812* (2013.01); *A61K 49/10* (2013.01); *C07F 5/003* (2013.01)

(58) Field of Classification Search
CPC ... C07F 5/003; A61K 49/126; A61K 49/1812; A61K 49/085; A61K 49/10
See application file for complete search history.

(56) References Cited

U.S. PATENT DOCUMENTS

| 8,361,708 | B2 | 1/2013 | Peiris et al. | |
| 2007/0189974 | A1* | 8/2007 | Takahashi | A61K 49/1812 424/9.365 |
| 2008/0267882 | A1 | 10/2008 | Chen et al. | |
| 2011/0288399 | A1 | 11/2011 | Herzka et al. | |
| 2012/0107232 | A1* | 5/2012 | Hsu | A61K 51/1234 424/1.21 |
| 2013/0219636 | A1* | 8/2013 | Dojan | D05B 53/00 12/142 R |
| 2016/0101197 | A1 | 4/2016 | Annapragada | |

OTHER PUBLICATIONS

Annapragada, et al., "Super-Relaxive Gd Nanoparticle," *Proc. International Society for Magnetic Resonance in Medicine*, 21: 3893, 2013.
Extended European Search Report Issued in Corresponding European Patent Application No. 17850396.7, dated May 6, 2020.
Ghaghada, et al., "High-Resolution Placental MR Angiography Using a Nanoparticle Contrast Agent," *Proc. International Society for Magnetic Resonance in Medicine*, 24: 749, 2016.
Ghaghada, et al., "New Dual Mode Gadolinium Nanoparticle Contrast Agent for Magnetic Resonance Imaging," *PLoS One*, 4(10): e7628-e7628, 2009.
Kang, et al., "$^{64}$Cu-Labeled Tetraiodothyroacetic Acid-Conjugated Liposomes for PET Imaging of Tumor Angiogenesis," *Nuclear Medicine and Biology*, 40: 1018-1024, 2013.
Zeng, et al., "Lipid AuNPs@PDA Nanohybrid for MRI/CT Imaging and Photothermal Therapy of Hepatocellular Carcinoma," *Applied Materials & Interfaces*, 6: 14266-14277, 2014.
Bednov et al., "L-arginine prevents hypoxia-induced vasoconstriction in dual-perfused human placental cotyledons" *Placenta*, 2015, 1254-1259.
Damodaram et al., "Placental MRI in Intrauterine Fetal Growth Restriction" *Placenta*, 2010, 31:491-498.
Di Bona et al., "Surface charge and dosage dependent potential developmental toxicity and biodistribution of iron oxide nanoparticles in pregnant CD-1 mice" *Reprod. Toxicol.*, 2014, 50:36-42.
Drummond et al., "Pharmacokinetics and in vivo drug release rates in liposomal nanocarrier development." *J. Pharm. Sci.*, 2008, 97(11):4696-4740.
Elsayes et al., "Imaging of the Placenta: a Multimodality Pictorial Review" *Radiographics: a review publication of the Radiological Society of North America*, 2009, 29(5):1371-1391.
Fraum et al., "Gadolinium-based contrast agents: A comprehensive risk assessment." *JMRI*, 2017, 46:338-353.
International Search Report and Written Opinion issued in Corresponding International Patent Application No. PCT/IB2017/055611, dated Mar. 5, 2018.

(Continued)

*Primary Examiner* — Michael G. Hartley
*Assistant Examiner* — Leah H Schlientz
(74) *Attorney, Agent, or Firm* — Norton Rose Fulbright US LLP

(57) ABSTRACT

The present invention is directed towards new chemical entities based on a lipid-paramagnetic metal ion chelate. The lipid portion of the compound intercalates into the membrane of a liposome. The compounds of the invention find particular use as paramagnetic contrast media for magnetic resonance imaging. It has been surprisingly discovered that the liposomal contrast media do not substantially cross the placental barrier into the vasculature of the fetus(es) when administered to a pregnant subject. These novel compounds are useful in the diagnosis of disorders and diseases in both gravid and non-gravid subjects. The invention is also directed towards pharmaceutical compositions comprising these compounds and the uses of these compounds.

19 Claims, 22 Drawing Sheets

(56) References Cited

OTHER PUBLICATIONS

Kakogawa et al., "Noninvasive monitoring of placental oxygenation by near-infrared spectroscopy." *American Journal of Perinatology*, 2010, 27(6):463-468.
Kakogawa et al., "Transabdominal Measurement of Placental Oxygenation by Near-infrared Spectroscopy" *American Journal of Perinatology*, 2010, 27(1):25-29.
Kawamura et al., "Measurement of placental oxygenation by transabdominal near-infrared spectroscopy" *American Journal of Perinatology*, 2007, 24(3):161-166.
Kulvietis et al., "Transport of nanoparticles through the placental barrier," *Tohoku J. Exp. Med.*, 2011, 225:225-234.
Ray et al., "Association Between MRI Exposure During Pregnancy and Fetal and Childhood Outcomes." *JAMA*, 2016, 316:952-961.
Shetty et al., "A liposomal Gd contrast agent does not cross the mouse placental barrier" *Scientific Reports*, 2016, 6.
Szoka & Papahadjopoulos, "Comparative properties and methods of preparation of lipid vesicles (liposomes)." *Ann. Rev. Biophys. Bioeng.*, 1980, 9:467-508.
Tache et al., "Hypoxia and Tropoblast Differentiation: a Key Role for PPARγ" *Stem Cells and Development*, 2013, 22(21):2815-2824.

\* cited by examiner

FIG. 5A-E

LIPOSOMAL GADOLINIUM (GD) CONTRAST AGENT "NMRX" FOR T1-MRI

This application is a national phase under 35 U.S.C. § 371 of International Application No. PCT/IB2017/055611, filed Sep. 15, 2017, which claims the benefit of priority to U.S. Provisional patent Application Ser. No. 62/395,836, filed Sep. 16, 2016, the entire contents of each of which are hereby incorporated by reference in their entirety.

FIELD OF THE INVENTION

The following relates to the medical arts, the obstetrics and gynecology arts, the medical imaging arts, and related arts.

BACKGROUND OF THE INVENTION

The placenta and umbilical cord are vital for proper growth and transfer of nutrients and gases to and from the fetus. Several conditions are related to abnormal function of placenta, including abnormal fetal growth, stillbirth, preeclampsia, and preterm birth (Haws et al., *BMC Pregnancy and Childbirth* 9 Suppl 1, S5 (2009); and Smith, G. C. and Fretts, R. C. *Lancet* 370(9600):1715-1725 (2007)). Current in vivo methods of fetal surveillance, including ultrasound tomography (UST) techniques and fetal heart rate monitoring, have proved to have low sensitivities and high false positive rates for adverse pregnancy outcomes (Grivell et al., *The Cochrane Database of Systematic Reviews*, 1:CD007113 (2009)).

Imaging of the placenta faces many limitations today. Fetal radiation exposure concerns contraindicate nuclear imaging and CT. Thus, ultrasound and Magnetic Resonance (MR) are the only currently viable options. Herzca et al. (U.S. Patent Application Publication No. 20110288399) disclose a method for detecting placental calcification. The method includes acquiring at least one magnetic resonance image of a placenta using an ultra-short echo time (UTE) pulse sequence; and processing the at least one magnetic resonance image to generate information indicative of placental calcification. Magnetic resonance imaging (MRI) and near infrared spectroscopy (NIRS) have been used experimentally to evaluate oxygenation, however, there are limitations in those approaches (Kakogawa et al., *American Journal of Perinatology*, 27(6):463-468 (2010); Kakogawa et al., *American Journal of Perinatology*, 24(3):161-166 (2007); Elsayes et al., *Radiographics: a review publication of the Radiological Society of North America, Inc.* 29(5): 371-1391 (2009)).

These techniques do not provide robust information on the development, blood flow to and within, and the integrity and function of the tissue in the placenta, which has important implications for both placental development as well as the development of conditions such as preeclampsia and intrauterine growth restriction (IUGR) (Tache et al., *Stem Cells and Development* (2013); Kakogawa et al., *American Journal of Perinatology*, 27(1):25-29 (2010)).

Abnormalities of placental development and function are known to underlie many major pathologies of pregnancy including spontaneous preterm birth, fetal growth restriction, and preeclampsia, and have seen significant increases in incidence in the last fifty years. For example, Placenta accreta and its related conditions (increta, percreta) have increased eight-fold, from 1 in 4000 births in the 1970's, to 1 in 500 in the last decade. Characterized by increasing degrees of placental invasion into the uterine wall, they are currently diagnosed by ultrasound or in special cases by MRI, in the setting of known risk factors. Sensitivity of detection however, is <80% overall, and while specificity is typically high (>90%), this still leaves a significant fraction of cases undetected, only discovered at childbirth. The standard-of-care is a mandatory Caesarean section often followed by a hysterectomy. If undiscovered, the placenta fails to separate from the uterus post-partum, resulting in massive obstetrical hemorrhage. Even with a planned Caesarean section, the ACOG reports that as many as 90% of placenta accreta patients require massive blood transfusions, and maternal mortality is as high as 7%. A circumstantial histological finding strongly predisposes the mother to the same condition on subsequent pregnancies.

Methods to safely characterize placenta accreta, placental permeability, and to molecularly profile the placenta in vivo, and longitudinally could greatly enhance our ability to study and treat placental dysfunction. Contrast agents are an obvious choice, but Gd contrast agents for T1-MR are generally contraindicated, for concerns related to fetal contrast agent exposure. Iron oxide nanoparticles for T2-MRI have been tried, but also penetrate the placental barrier. The lack of acceptable MRI contrast agents greatly limits what can be achieved by placental MR imaging. Di Bona, K. R. et al. Surface charge and dosage dependent potential developmental toxicity and biodistribution of iron oxide nanoparticles in pregnant CD-1 mice. *Reprod. Toxicol.* 50, 36-42 (2014); and Kulvietis, V., et al. Transport of nanoparticles through the placental barrier. *Tohoku J. Exp. Med.* 225, 225-234 (2011).

Thus, there is a need in the art for improved methods of assessing placental development and function in vivo. Particularly, a need exists for cost effective contrast agents usable with current methods of magnetic resonance imaging for a real time assessment of the developing placenta and umbilical cord. The present invention fulfills this longstanding need and desire in the art.

SUMMARY OF THE INVENTION

In various embodiments, the present invention provides a paramagnetic nanoparticular, e.g., liposomal, contrast medium with beneficial properties in diagnostic imaging studies of pregnant subjects. The contrast agents are of use in methods for characterizing the placenta, including in methods for studying placental perfusion, and molecular profiles in the context of both normal placenta and placental pathologies. The broad utility of contrast enhanced MRI and MR Molecular Imaging has not been exploited for such applications due to concerns regarding fetal exposure to contrast media. The biocompatible, substantially non-toxic contrast media of the present invention mitigate these concerns.

An exemplary contrast medium of the invention includes a paramagnetic metal chelate formed between a chelating agent, (e.g., a macrocyclic chelating agent) and a paramagnetic metal ion, e.g., Gd(III). The paramagnetic metal chelate is incorporated into a liposomal membrane through a lipid moiety conjugated to the chelating agent. Contrast media of the invention, when administered to a pregnant subject, remain largely confined within the maternal vasculature; the contrast agents do not significantly pass the placenta to enter into the vasculature of the fetus(es). For the first time, it is possible to acquire contrast enhanced images of a pregnant subject and assess the development and viability of the placenta using this modality without significant risk of distributing the contrast media into the vasculature of the fetus(es).

The ability of the contrast agents of the invention to distribute and remain confined within the maternal vasculature is largely due to the liposomes in which the paramagnetic metal ion chelate is contained. Liposomes are vesicle structures usually composed of a bilayer membrane of amphipathic molecules such as, phospholipids, entrapping an aqueous core. The diameters and morphology of various types of liposomes are known in the art. (D. Drummond et al., *J. Pharm. Sci.,* (2008) 97(11):4696-4740, PMID 10581328).

The agent provides superb blood pool contrast, enabling visualization of tiny blood vessels and vascular leak. An exemplary agent is able to detect vessels as small as about 100 µm diameter vessels easily. Thus, NMRX enables detailed studies of the uterine vasculature, throughout pregnancy.

Other embodiments, objects and advantages of the invention will be apparent from the detailed description that follows.

DETAILED DESCRIPTION OF THE INVENTION

Figure 1:
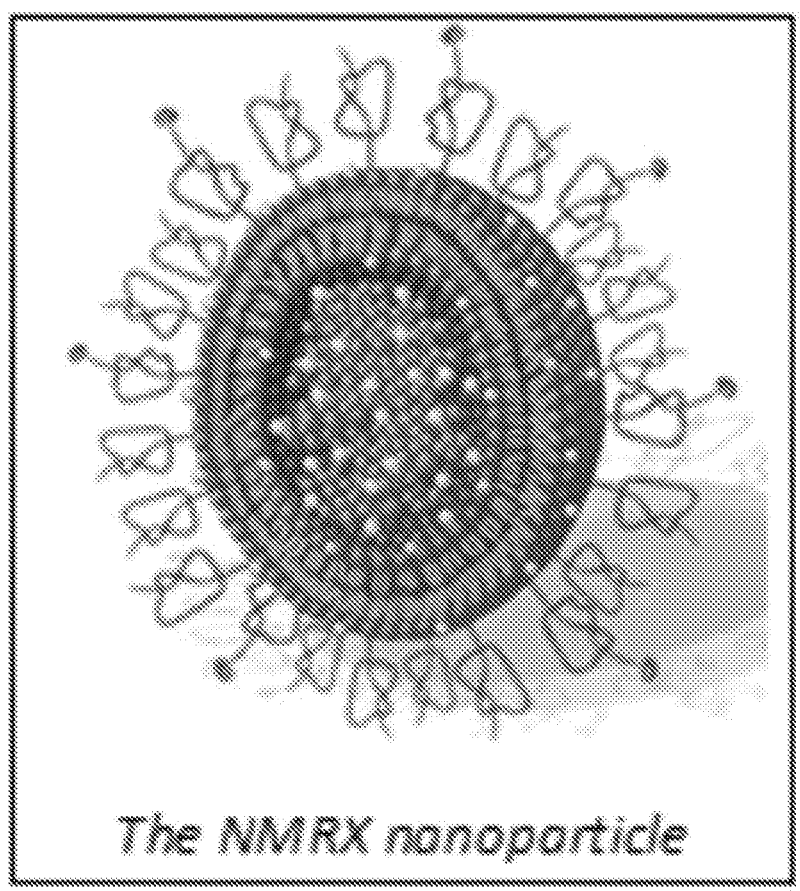
FIG. 1. An exemplary NMRX nanoparticle presents gadolinium in a stable liposomal nanoparticle with very low permeability across the placental membrane thereby minimizing or eliminating toxicity to the fetus.

Reference will now be made in detail to exemplary compositions, embodiments and methods of the present invention which constitute the best modes of practicing the invention presently known to the inventors. It is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Introduction

Within the field of diagnostic medical imaging, as exemplified by magnetic resonance imaging (MRI), there remains a need for biocompatible, substantially non-toxic contrast media with novel and useful properties. Of particular interest are contrast agents based on paramagnetic metal ion chelates that have improved pharmacokinetic and toxicity profiles. This concern is particularly pertinent and timely with respect to lanthanide ion-based contrast media, e.g., Gd(III)-based media, which have been demonstrated to be toxic in certain subjects. Due to the potential toxicity of these versatile, diagnostically valuable agents, they have not been extended to use in imaging pregnant subjects. Thus, the high diagnostic yield available via contrast enhanced MRI is not available to subjects who are pregnant. As disclosed herein, the present invention has mitigated the difficulties associated with the use of MR contrast media in imaging studies of pregnant subjects.

Definitions

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

The following definitions are broadly applicable to each of the embodiments of the present invention set forth herein below. Unless defined otherwise, all technical and scientific terms used herein generally have the same meaning as commonly understood by one of ordinary skill in the art to which this invention belongs. Generally, the nomenclature used herein and the laboratory procedures in analytical chemistry, and organic synthesis are those well-known and commonly employed in the art. Standard techniques, or modifications thereof, are used for chemical syntheses and chemical analyses.

The term "alkyl," by itself or as part of another substituent, means, unless otherwise stated, a straight- or branched-chain, or cyclic hydrocarbon radical, or combination thereof, which is fully saturated and can include mono-, di-, tri- and tetra-valent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. The term "alkyl", as used herein refers to alkyl moieties, which can be mono-, di- or polyvalent species as appropriate to satisfy valence requirements.

The term "alkenyl," by itself or as part of another substituent, means, unless otherwise stated, a straight- or branched-chain, or cyclic alkyl radical, or combination thereof, having one or more carbon-carbon double bonds. Examples of alkenyl groups include, but are not limited to, vinyl, 2-propenyl, crotyl, isopenten-2-yl, butadien-2-yl, 2,4-pentadienyl, 1,4-pentadien-3-yl, and the higher homologs and isomers.

The term "alkynyl," by itself or as part of another substituent, means, unless otherwise stated, a straight- or branched-chain, or cyclic alkyl radical, or combination thereof, having one or more carbon-carbon triple bonds. Examples of alkynyl groups include, but are not limited to, ethynyl, 1- and 3-propynyl, 3-butynyl, and the higher homologs and isomers.

The term "alkylene," by itself or as part of another substituent, means a divalent radical derived from an alkyl moiety, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present invention. For alkylene and heteroalkylene linker groups, it is optional that no orientation of the linker group is implied by the direction in which the formula of the linker group is written. For example, the formula —$C(O)_2R'$— represents —$C(O)_2R'$— and, optionally, —$R'C(O)_2$—. A "lower alkyl" or "lower alkylene" is a shorter chain alkyl or alkylene group, generally having eight, seven, six, five or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus, e.g., the position through which the alkyl group is attached to the remainder of the molecule. Examples of "heteroalkyl" groups include, but are not limited to, —$CH_2$—$CH_2$—O—$CH_3$, —$CH_2$—$CH_2$—NH—$CH_3$, —$CH_2$—$CH_2$—$N(CH_3)$—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —$Si(CH_3)_3$, and —$CH_2$—CH=N—$OCH_3$. Two or more heteroatoms may be consecutive, such as, for example, —$CH_2$—NH—$OCH_3$ and —$CH_2$—O—$Si(CH_3)_3$. Similarly, the term "heteroalkylene" by itself or as part of another substituent refers to a divalent heteroalkyl radical, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the termini (e.g., alkyleneoxy, alkylenedioxy, alkyleneamino, alkylenediamino, and the like). An exemplary heteroalkyl moiety is interrupted by one or more ring structure, e.g., heterocycloalkyl or heteroaryl rings formed in which a ring joins a carbon or a heteroatom of the heteroaryl moiety.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, cycloheptyl, and the like. Examples of heterocycloalkyl include, but are not limited to, 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

In some embodiments, any of the alkyl, alkenyl, alkynyl, alkylene, heteroalkylene, alkoxy, alkylamino, alkylthio, heteroalkyl, cycloalkyl and heterocycloalkyl groups is optionally substituted, e.g., with one or more groups referred to herein as an "alkyl group substituent."

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic substituent that can be a single ring or multiple rings (preferably from 1 to 3 rings), which are fused together. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. In some embodiments, any of the aryl and heteroaryl groups is optionally substituted, e.g., with one or more groups referred to herein as an "aryl group substituent."

The term "arylalkyl" includes those radicals in which an aryl group is attached to an alkyl group (e.g., benzyl, phenethyl, and the like).

Substituents for the alkyl and heteroalkyl radicals as well as those groups often referred to as alkylene, heteroalkylene, alkenyl, heteroalkenyl, alkynyl, cycloalkyl, heterocycloalkyl, cycloalkenyl, and heterocycloalkenyl are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "substituted alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." Exemplary substituents are selected from the list of alkyl group substituents and others, for example: halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on an aryl or heteroaryl ring, together with the atom to which they are attached, may optionally be joined to form a ring (e.g., a cycloalkyl or heterocycloalkyl ring) that is fused to the aryl or heteroaryl ring.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_{16}$)alkyl.

As used herein, the term "heteroatom" includes oxygen (O), nitrogen (N), sulfur (S) and silicon (Si).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocyclyl groups. R can also refer to alkyl group substituents and aryl group substituents.

The symbol ⟿, displayed perpendicular to a bond, indicates the point at which the displayed moiety is attached to the remainder of the molecule.

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The term "charged group" refers to a group that bears a negative charge or a positive charge. The negative charge or positive charge can have a charge number that is an integer selected from 1, 2, 3 or higher or that is a fractional number. Exemplary charged groups include for example —$OPO_3^{2-}$, —$OPO_2^-$, —$P^+Ph_3$, —$N^+R'R''R'''$, —$S^+R$ and —$C(O)O^-$. It is understood that charged groups are accompanied by counterions of opposite charge, whether or not such counterions are expressly represented in the formulae provided herein.

The compounds herein described may have one or more charged groups. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as $Na^+$, $Ca^{++}$, $Mg^{++}$, or $K^+$ hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated.

The term "biocompatible", as used herein, refers to an object, material, or composition that is substantially non-toxic and non-immunogenic. More broadly, biocompatibility is the ability of a material to perform with an appropriate host response in a specific situation. Therefore, biocompatibility represents a global statement on how well body tissues interact with a material and how this interaction meets the designed expectation for a certain implantation purpose and site [See, Von Recum, A. F., et al., "Introduction: Biomaterials and Biocompatibility.", in: Handbook of Biomaterials Evaluation: Scientific, Technical and Clinical Testing of Implant Materials. von Recum, A. F., Ed.; Taylor & Francis, 1999: pp. 1-8]. Hence, biocompatibility is a relative rather than an absolute concept, which depends to a large degree on the ultimate expectation of the material.

The term "substantially non-toxic", as used herein, means a surface or material this is substantially non-hemolytic and substantially, meaning that the surface, material or composition does not leach a sufficient amount of the imaging agent or other compositions as described herein to generate a toxic reaction in a host from the released material.

The term "diagnostically effective amount", as used herein, refers to an amount of a composition of the invention effective to diagnose a disease or disorder in a subject.

The term "MRI" is used herein as an abbreviation for "magnetic resonance imaging". The terms "MRI" and "magnetic resonance imaging" are used interchangeably in the following disclosure. The terms "MRI magnetic environment" and "MRI environment" are used to refer to the powerful magnetic field created by MRI magnets which are a component of MRI systems. The MRI magnetic environment typically contains all or part of a patient's body when that body undergoes MRI imaging. Further, it is expected that during the life of this patent many relevant techniques for magnetic resonance imaging will be developed, and the scopes of the terms "MRI" and "magnetic resonance imaging" are intended to include all such new technologies a priori.

As used herein, the term "about" refers to +/−10%.

The term "chelating agent" as used herein refers to any organic or inorganic compound that will bind to a metal ion having a valence greater than one. "Chelating agents" include, but are not limited to, macrocyclic organic chelating agents such as 1,4,7,10-tetraazacyclododecane-1,4,7,10-tetraacetic acid (DOTA), and 1,4,8,11-tetraazacyclotetradecane-N,N',N'',N'''-tetraacetic acid (TETA). See, e.g., Kaden, T A. Host Guest Complex Chemistry III, Volume 121 of the series Topics in Current Chemistry pp 157-179 (2005). Open chain chelators are also included under this definition, e.g., ethylenediamenetetracetic acid (EDTA), triethylene tetramine dihydrochloride (TRIEN), ethylene glycol-bis (.quadrature.-aminoethyl) ether-N,N,N',N'-tetracetic acid (EGTA), diethylenetriamin-pentaacetic acid (DPTA), and triethylenetetramine hexaacetic acid (TTG), deferoxamine, dimercaprol, edetate calcium disodium, zinc citrate, penicillamine succimer and editronate, or any other chelating agent that will chelate divalent and trivalent ions and which are biologically compatible with administration to a mammalian subject, e.g., a pregnant subject. The chelate is optionally in the form of a salt, e.g., a pharmaceutically acceptable salt.

The term "linker" or "linker group", as used herein, relates to moieties which are attached to the chelating group, joining it to a lipid moiety that intercalates within the liposome membrane, and which have at least one functional group which is capable of covalently binding to (or had bound to) a lipid moiety that interacts with the lipid membrane. Where linkers or chelating agents have a plurality of such functional groups, they may be the same or different. When the chelating moiety is macrocyclic, the linker moiety may be attached to any annular atom. For example, when the chelating moiety is a polyazamacrocycle, the pendant group may be attached to an annular carbon atom or an annular nitrogen atom. When the pendant group is attached to an annular nitrogen atom, the compound may be referred to as an N-substituted polyazamacrocycle. Exemplary linkers are alkylene, alkenyl, and alkynyl groups as well as these groups including one or more heteroatoms, such that the groups are heteroalkylene, heteroalkenyl and heteroalkynyl groups. A linker can also be a bond or a moiety formed by the reaction of complementary functional groups on, e.g., a phospholipid moiety and a PEG moiety.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate, and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. Hydrates of the salts are also included.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zunch, Switzerland: 2002). The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, flimarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

The phrase "pharmaceutical formulation" refers to a formulation of a compound and a medium generally accepted in the art for the delivery of the diagnostic compound to mammals, e.g., humans. Such a medium includes all pharmaceutically acceptable carriers, diluents or excipients therefore.

The phrase "pharmaceutically acceptable carrier, diluent or excipient" as used herein includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

EXEMPLARY EMBODIMENTS

In exemplary embodiments of the invention, there is provided a biocompatible, substantially non-toxic contrast agent based on a nanoparticle ("NMRX"), in contrast to conventional contrast agents, which are based on small molecules. The non-permeability of the nanoparticles of the invention is unexpected and novel. The low permeability allows only extremely low amounts of the contrast agent from crossing over the placental barrier into the fetal circulation. An exemplary nanoparticulate contrast medium is shown in FIG. 1.

In various embodiments, the invention provides a compound according to Formula I:

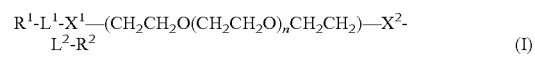

$$R^1\text{-}L^1\text{-}X^1\text{—}(CH_2CH_2O(CH_2CH_2O)_nCH_2CH_2)\text{—}X^2\text{-}L^2\text{-}R^2 \quad (I)$$

wherein $R^1$ is a phospholipid; $L^1$ and $L^2$ are linkers independently selected from a bond, substituted or unsubstituted alkyl, and substituted or unsubstituted heteroalkyl; $X^1$ and $X^2$ are independently selected from 0 and NH; n is an integer from 5 to 500; and $R^2$ is a paramagnetic metal ion chelate comprising a macrocyclic ligand complexing a paramagnetic metal ion, said chelate having a thermodynamic stability constant (log $K_{GdL}$) of at least about 20, e.g., at least about 22, e.g., at least about 24.

Any useful paramagnetic metal ion chelate can be used. In an exemplary embodiment, the compound of the invention includes a macrocyclic ligand is a tetraaza macrocycle. Exemplary macrocyclic ligands complexed to Gd(III) include:

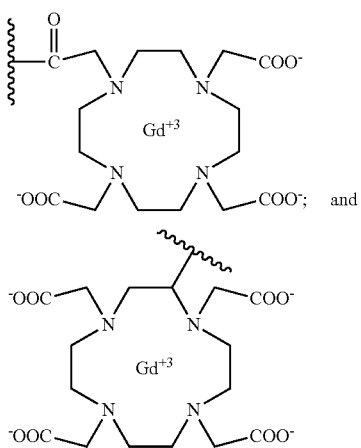

and

In according with Formula I, in exemplary compounds of the invention, the phospholipid is:

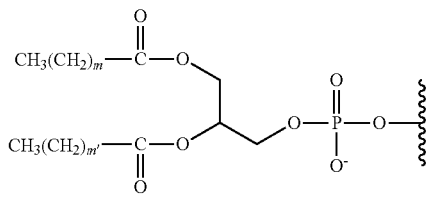

wherein m and m' are independently selected integers from 4 to 24. Exemplary values for m and m' include the integers from 10, 11, 12, 13, 14, 15, 16, 17, 18, 19, 20, 21 and 22.

$L^1$ is an exemplary linker moiety joining the phospholipid to the PEG moiety in the compounds according to Formula I. As will be appreciated by those of skill in the art, $L^1$ is a linker with any convenient and appropriate structure. Exemplary moieties for $L^1$ include:

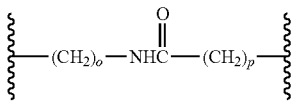

wherein o and p are independently selected from the integers 0, 1 and 2.

In exemplary compounds according to Formula I, $R^1$-$L^1$ is:

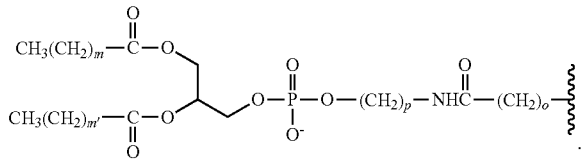

Similar to $L^1$, in exemplary compounds according to Formula I, the moiety $L^2$ is a linker of any appropriate and convenient structure. Exemplary species for $L^2$ include:

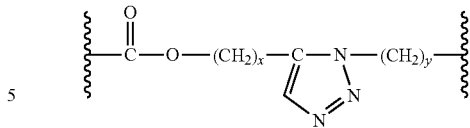

wherein x and y are independently selected from the integers 0, 1, and 2.

In an exemplary embodiment, $L^2$-$R^2$ is:

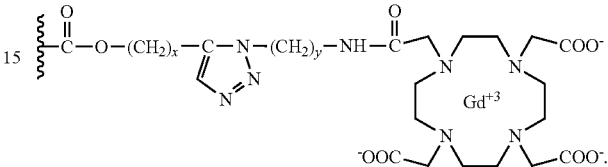

Figure 2:
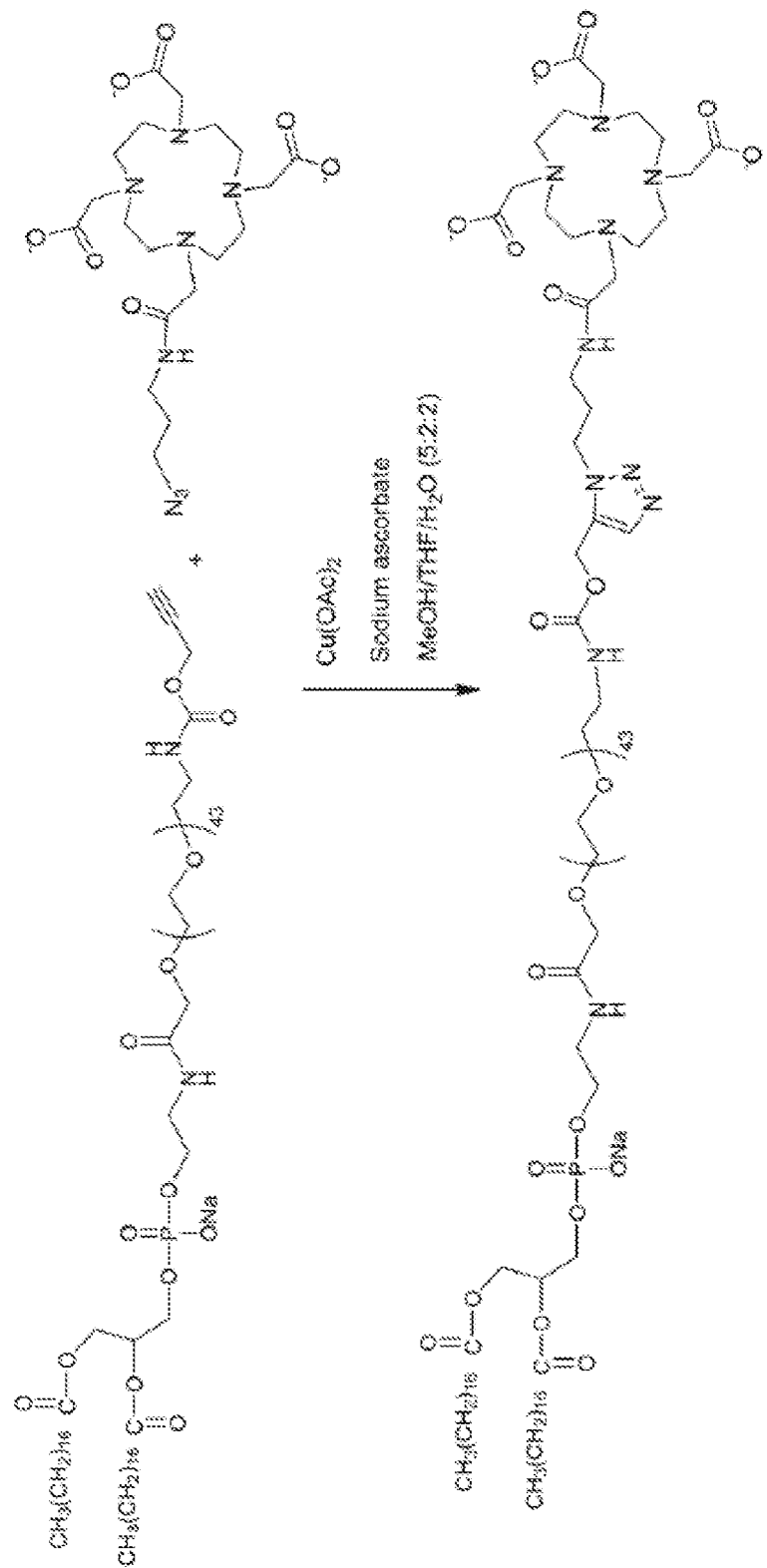
FIG. 2. A synthetic route to an exemplary lipid-chelate conjugate of the invention.

The paramagnetic metal chelate-lipid component of the contrast media of the invention are readily prepared using art-standard methods and available reagents and precurosors. FIG. 2. Exemplary contrast media are based on macrocyclic chelating agents complexed with a paramagnetic ion to form highly stable chelates. The use of such highly stable greatly reduces concerns about nephrogenic systemic fibrosis and brain deposition, side-effects of Gd contrast agents.

Liposomes

In various embodiments, the invention provides novel liposomal paramagnetic contrast agents for MRI studies, e.g., T1-MRI, of a pregnant subject, substantially retaining the Gd on the maternal side, without penetrating the placental barrier, thus shielding the fetus(es) from the contrast agent and any potential toxicity originating therefrom. In various embodiments, a sufficient amount of the paramagnetic contrast agent is retained on the maternal side to obviate or significantly reduce clinical concerns regarding exposure of the fetus(es) to the contrast medium. In various embodiments, not more than about 10%, 9%, 8%, 7%, 6%, 5%, 4%, 3%, 2% or not more than about 1% of the dose administered to the pregnant subject traverses the placenta to enter the vasculature of the fetus(es).

Exemplary liposomes include the lipid-paramagnetic chelate conjugate of Formula I as a first lipid component of the liposome. In various embodiments, the liposomes further comprises a second lipid component of the liposome membrane.

Other than including as a component a chelating agent conjugated lipid of the invention, membrane components of the liposome of the present invention are not particularly limited. Exemplary liposomal membranes useful in the current invention may be formed from a variety of vesicle-forming lipids, typically including dialiphatic chain lipids, such as phospholipids, diglycerides, dialiphatic glycolipids, single lipids such as sphingomyelin and glycosphingolipid, cholesterol and derivates thereof, and combinations thereof. As defined herein, phospholipids are amphiphilic agents having hydrophobic groups formed of long-chain alkyl chains, and a hydrophilic group containing a phosphate moiety. The group of phospholipids includes phosphatidic acid, phosphatidyl glycerols, phosphatidylcholines, phosphatidylethanolamines, phosphatidylinositols, phosphatidylserines, and mixtures thereof. Exemplary phospholipids are chosen from 1,2-dipalmitoyl-sn-glycero-3-phosphocholine (DPPC), dimyristoyl-phosphatidylcholine (DMPC), hydrogenated soy phosphatidylcholine (HSPC), soy phosphatidylcholine (SPC), dimyristoylphosphatidylglycerol (DMPG), disrearoylphosphatidylglycerol (DSPG), 1-palmitoyl-2-oleoyl-sn-glycero-3-phosphocholine (POPC), 1,2-dioleoyl-sn-glycero-3-phosphocholine (DOPC), distearoyl phosphatidylcholine (DSPC), egg yolk phosphatidylcholine (EYPC) or hydrogenated egg yolk phosphatidylcholine (HEPC), sterol modified lipids (SML), cationic lipids and inverse-zwitterlipids.

In various embodiments, the second lipid component is selected from distearoyl phosphatidylcholine (DSPC), 1,2-dipalmitoyl-sn-glycero-3-phosphocholine (DPPC), hydrogenated soy phosphatidylcholine (HSPC), cholesterol, 1,2-distearoyl-sn-glycero-3-phosphoethanolamine-mPEG (DSPE-mPEG) and a combination thereof.

The components of the liposome of the present invention are not limited to the aforementioned components, and other components may be added. Examples of such components include cholesterol, cholesterol esters, sphingomyelin, monosial ganglioside GM1 derivatives described in *FEBS Lett.*, 223, 42 (1987); *Proc. Natl. Acad. Sci., USA,* 85, 6949 (1988) etc., glucuronic acid derivatives described in *Chem. Lett.*, 2145 (1989); *Biochim. Biophys. Acta*, 1148, 77 (1992) etc., polyethylene glycol derivatives described in *Biochim. Biophys. Acta,* 1029, 91 (1990); *FEBS Lett.,* 268, 235 (1990) and the like. However, the components are not limited to these examples.

Exemplary embodiments of the present invention provide contrast media based on a type of art-recognized liposome, the Stealth liposome. Stealth liposomes have well understood pharmacokinetics, organ distribution and safety profiles. These liposomes generally include at least one PEGylated lipid incorporated into the liposomal lipid membrane. Stealth liposomes according to the present invention have been demonstrated, in various rodent species and perfused human placentae, to not penetrate the placental barrier, thus preventing fetal exposure, thereby improving fetal safety in contrast enhanced MRI studies in pregnant subjects.

An exemplary liposome of the invention comprises:
(i) about 1% to about 15% of a lipid according to claim 1;
(ii) about 50% to about 60% matrix lipid selected from distearoyl phosphatidylcholine (DSPC), 1,2-dipalmitoyl-sn-glycero-3-phosphocholine (DPPC), hydrogenated soy phosphatidylcholine (HSPC) and a combination thereof;
(iii) about 10% to about 40% cholesterol; and
(iv) about 1% to about 5% 2-distearoyl-sn-glycero-3-phosphoethanolamine-mPEG (DSPE-mPEG).

Figure 3A:
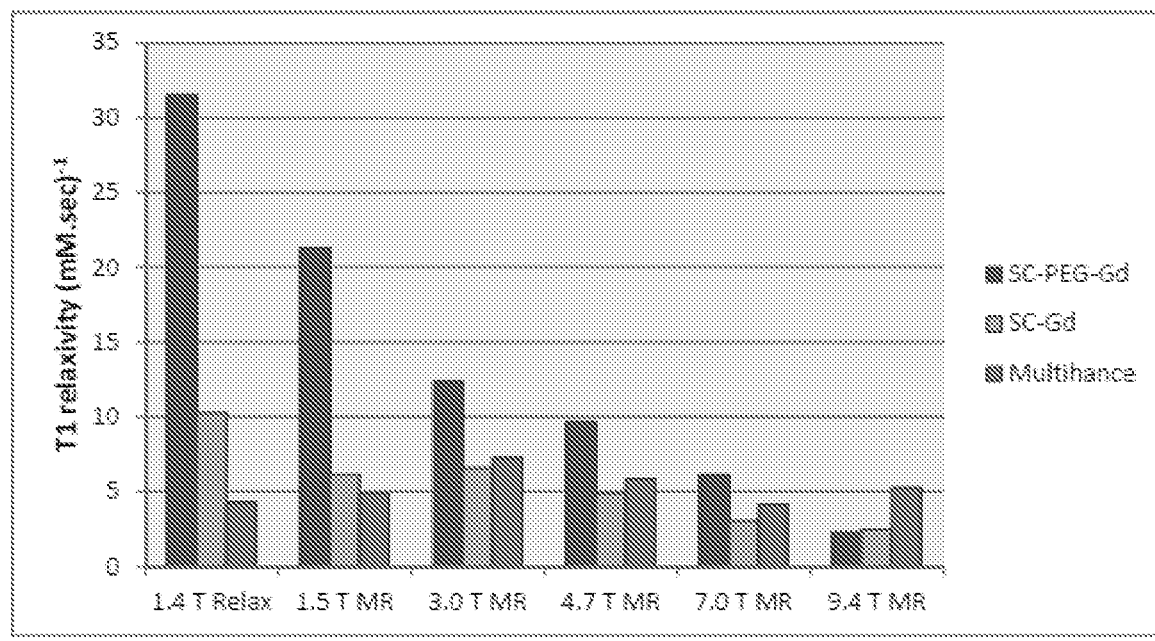
FIG. 3A. Nanoparticles formulated with novel PEG-Gd conjugate show superior relaxivity over existing constructs.
Figure 3B:
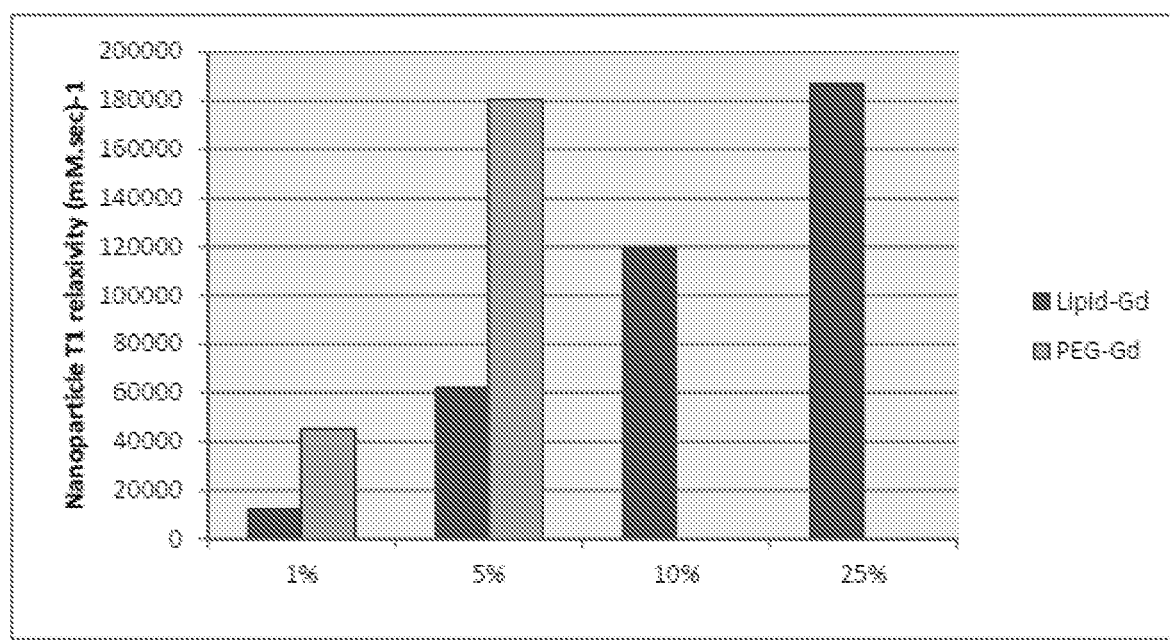
FIG. 3B. Nanoparticles formulated with novel PEG-Gd conjugate show superior relaxivity over existing constructs.

Liposomal MRI contrast media of the instant invention demonstrate remarkably high relaxivity at low field (1-3T) (FIGS. 3A and 3B). In an exemplary liposome of the invention, the paramagnetic chelate has a T1 relaxivity at about 1 to about 3 Tesla, which is at least about 4- to about 8-times greater than the same paramagnetic chelate not incorporated into said liposome.

Figure 4:
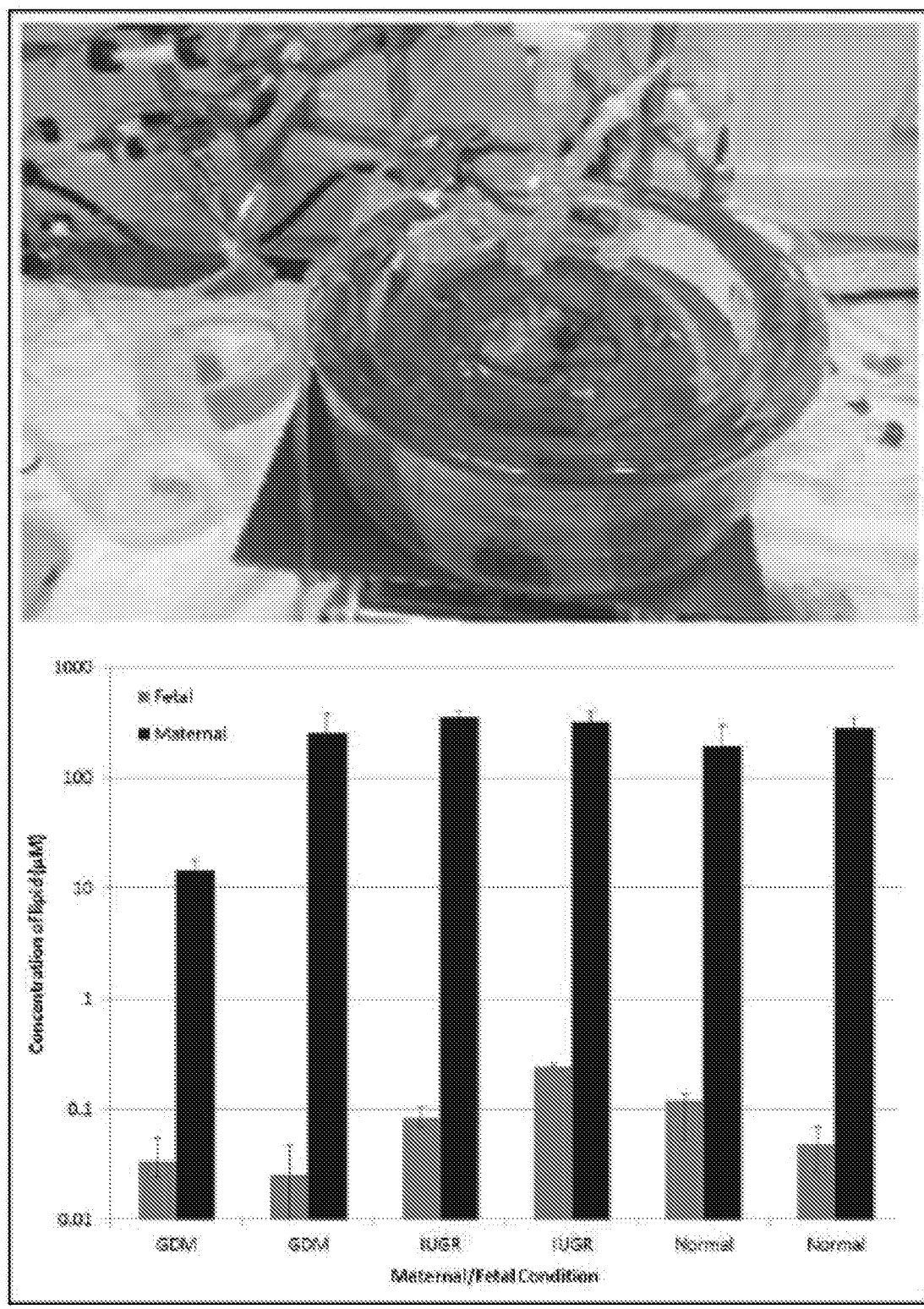
FIG. 4. In vitro testing shows no statistically significant amounts of NMRX-borne Gd crosses the placenta membrane from mother to fetal side.
Figure 5:
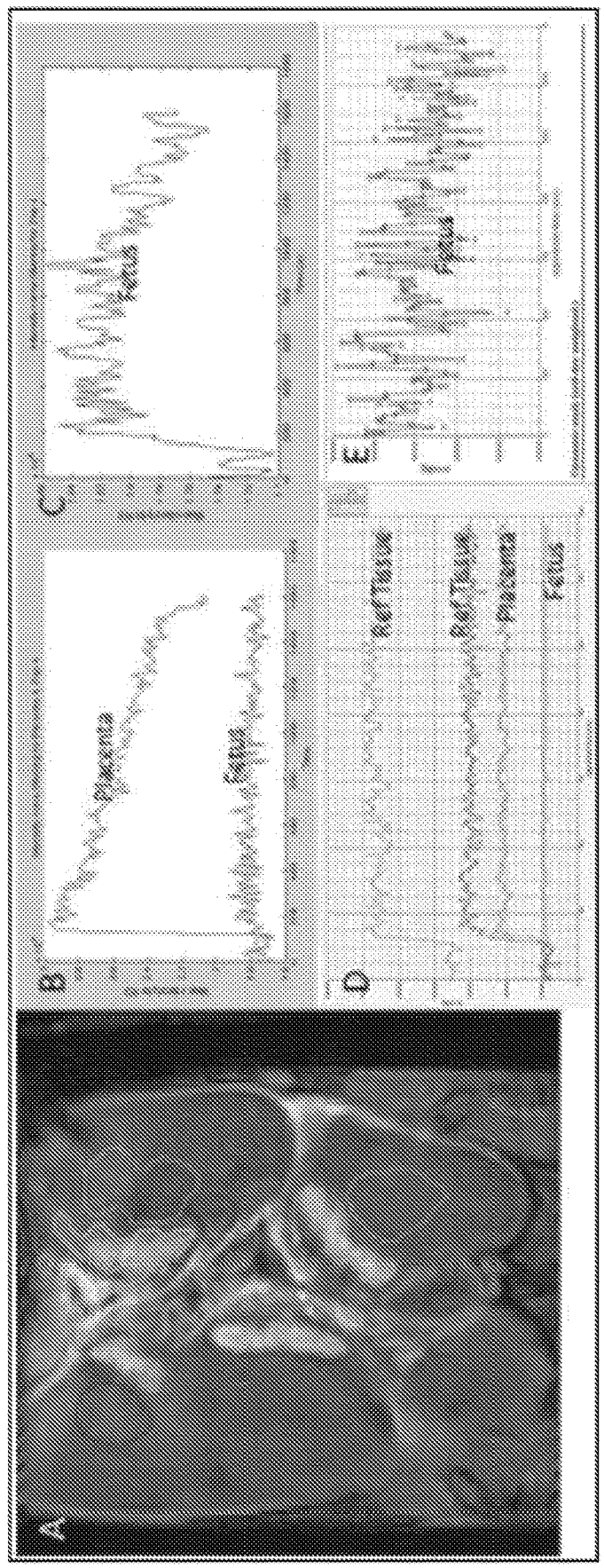
FIGS. 5A-E. In vivo testing by MRI shows NMRX have easy access to placenta but do not cross over to the fetus.
Figure 6:
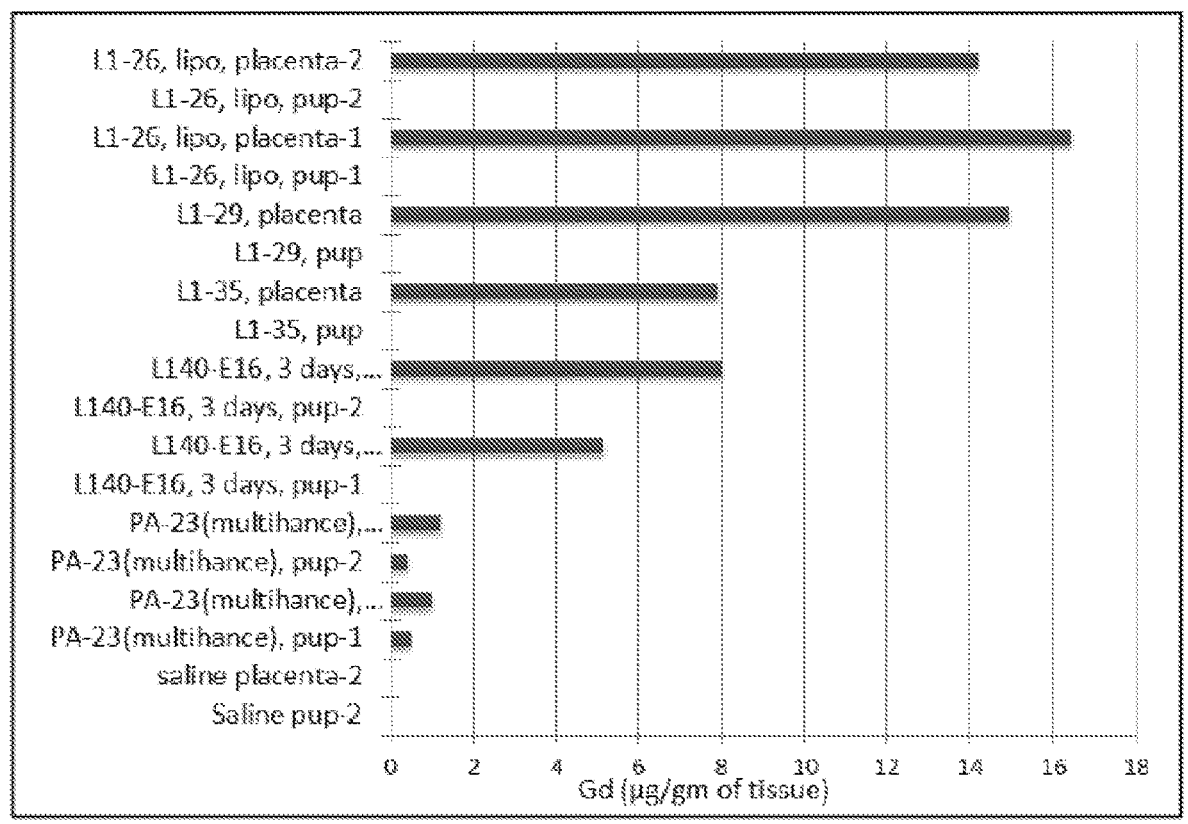
FIG. 6. Tissue analysis confirms that no statistically significant amounts of NMRX Gd reaches fetal tissue.

Exemplary Gd-containing liposomes of the invention show ultra-high relaxivity and do not significantly penetrate the placental barrier (FIG. 4, FIG. 5 and FIG. 6). Neither the lipid nor the aqueous payload penetrate the placental barrier. In various embodiments, this non penetration is demonstrated in ex vivo human perfused placentae and in rodent placentae in vivo.

As shown in the Examples included in the instant application, substantial confinement of the liposome and the paramagnetic chelate component of the liposome to the maternal circulation is demonstrable in pregnant mice, pregnant rats, and perfused human placentae from normal and abnormal pregnancies.

In various embodiments, one or more agent, in addition to the Gd-based contrast agent is incorporated into the liposomes. For example, in an exemplary embodiment, a contrast agent for a modality other than MRI is included in the liposome, e.g., an agent for fluorescence imaging, or near infrared fluorescence imaging. In an exemplary embodiment, the liposome also includes an iodinated compound for CT. Exemplary liposomal formulations of the invention also include a therapeutic molecule for drug delivery with image guidance.

The term liposome is used herein in accordance with its usual meaning, referring to microscopic lipid vesicles composed of a bilayer of phospholipids or any similar amphipathic lipids encapsulating an internal aqueous medium. The liposomes of the present invention can be unilamellar vesicles such as small unilamellar vesicles (SUVs) and large unilamellar vesicles (LUVs), and multilamellar vesicles (MLV), typically varying in size from 30 nm to 200 nm. No particular limitation is imposed on the liposomal membrane structure in the present invention. The term liposomal membrane refers to the bilayer of phospholipids separating the internal aqueous medium from the external aqueous medium.

The liposome of the contrast medium of the present invention can be prepared by any method known in the field of the art. Examples of the preparation method are described in the references as general review of liposomes, which are mentioned above, as well as in *Ann. Rev. Biophys. Bioeng.,* 9, 467 (1980), "Liopsomes" (Ed. by M. J. Ostro, MARCELL DEKKER, INC.) and the like. Specific examples include, but not limited thereto, the ultrasonication method, ethanol injection method, French press method, ether injection method, cholic acid method, calcium fusion method, freeze and thawing method, reverse phase evaporation method and the like. Size of the liposome of the present invention may be any of those obtainable by the aforementioned methods. Structure of the liposome is not particularly limited, and may be unilamellar or multilamellar structure.

In accordance with the invention, liposomes can be prepared by any of the techniques now known or subsequently developed for preparing liposomes. For example, the liposomes can be formed by the conventional technique for preparing multilamellar lipid vesicles (MLVs), that is, by depositing one or more selected lipids on the inside walls of a suitable vessel by dissolving the lipids in chloroform and then evaporating the chloroform, and by then adding the aqueous solution which is to be encapsulated to the vessel, allowing the aqueous solution to hydrate the lipid, and swirling or vortexing the resulting lipid suspension. This process engenders a mixture including the desired liposomes. Alternatively, techniques used for producing large unilamellar lipid vesicles (LUVs), such as reverse-phase evaporation, infusion procedures, and detergent dilution, can be used to produce the liposomes. A review of these and other methods for producing lipid vesicles can be found in the text Liposome Technology, Volume I, Gregory Gregoriadis Ed., CRC Press, Boca Raton, Fla., (1984), which is incorporated herein by reference. For example, the lipid-containing particles can be in the form of steroidal lipid vesicles, stable plurilamellar lipid vesicles (SPLVs), monophasic vesicles (MPVs), or lipid matrix carriers (LMCs). In the case of MLVs, if desired, the liposomes can be subjected to multiple (five or more) freeze-thaw cycles to enhance their trapped volumes and trapping efficiencies and to provide a more uniform interlamellar distribution of solute.

Following liposome preparation, the liposomes are optionally sized to achieve a desired size range and relatively narrow distribution of liposome sizes. A size range of about 20-200 nanometers allows the liposome suspension to be sterilized by filtration through a conventional filter, typically a 0.22 or 0.4 micron filter. The filter sterilization method can be carried out on a high through-put basis if the liposomes have been sized down to about 20-200 nanometers. Several techniques are available for sizing liposomes to a desired size. Sonicating a liposome suspension either by bath or probe sonication produces a progressive size reduction down to small unilamellar vesicles less than about 50 nanometer in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 50 and 500 nanometers, are observed. In both methods, the particle size distribution can be monitored by conventional laser-beam particle size determination. Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. Alternatively controlled size liposomes can be prepared using microfluidic techniques wherein the lipid in an organic solvent such as ethanol or ethanol-aprotic solvent mixtures is rapidly mixed with the aqueous medium, so that the organic solvent/water ratio is less than 30%, in a microchannel with dimensions less than 300 microns and preferable less than 150 microns in wide and 50 microns in height. The organic solvent is then removed from the liposomes by dialysis. Other useful sizing methods such as sonication, solvent vaporization or reverse phase evaporation are known to those of skill in the art.

The internal aqueous medium, as referred to herein, typically is the original medium in which the liposomes were prepared and which initially becomes encapsulated upon formation of the liposome. Embodiments are also envisaged, however, wherein the liposomes, after preparation, are dehydrated, e.g. for storage. Liposomes are optionally dehydrated under reduced pressure using standard freeze-drying equipment or equivalent apparatus. In various embodiments, the liposomes and their surrounding medium are frozen in liquid nitrogen before being dehydrated and placed under reduced pressure. To ensure that the liposomes will survive the dehydration process without losing a substantial portion of their internal contents, one or more protective sugars are optionally employed to interact with the lipid vesicle membranes and keep them intact as the water in the system is removed. A variety of sugars can be used, including such sugars as trehalose, maltose, sucrose, glucose, lactose, and dextran. In general, disaccharide sugars have been found to work better than monosaccharide sugars, with the disaccharide sugars trehalose and sucrose being most effective. Other more complex sugars can also be used. For example, aminoglycosides, including streptomycin and dihydrostreptomycin, have been found to protect liposomes during dehydration. Typically, one or more sugars are included as part of either the internal or external media of the lipid vesicles. Most preferably, the sugars are included in both the internal and external media so that they can interact with both the inside and outside surfaces of the liposomes' membranes. Inclusion in the internal medium is accomplished by adding the sugar or sugars to the buffer which becomes encapsulated in the lipid vesicles during the liposome formation process. In these embodiments the external medium used during the active loading process should also preferably include one or more of the protective sugars As is generally known to those skilled in the art, polyethylene glycol (PEG)-lipid conjugates have been used extensively to improve circulation times for liposome-encapsulated functional compounds, to avoid or reduce premature leakage of the functional compound from the liposomal composition and to avoid detection of liposomes by the body's immune system. Hence, in an exemplary embodiment of the invention, the liposomes are PEGylated liposomes. PEGylation can be accomplished by incorporating a PEGylated lipid into the liposomes. Suitable PEG-derived lipids according to the invention, include conjugates of DSPE-PEG, in which the molecular weight of PEG is between 2000 and 5000 g/mol. Other suitable PEG-derived lipids are mPEGs conjugated with ceramide, having either $C_8$- or $C_{16}$-tails, in which the molecular weight of mPEG is between 750 and 5000 daltons. Still other appropriate ligands are mPEGs or functionalized PEGs conjugated with glycerophospholipds like 1,2-dimyristoyl-sn-glycero-3-phosphoethanolamine (DMPE), 1,2-dipalmitoyl-sn-glycero-3-phosphoethanolamine (DPPE), 1,2-dioleoyl-sn-glycero-3-phosphoethanolamine (DOPE) and 1,2-distearoyl-sn-glycero-3-phosphoethanolamine (DSPE), and the like. Formation of PEGylated liposomes is a technique generally known by those skilled in the art.

In various embodiments, the liposomes are PEGylated with DSPE-PEG-GSH conjugates (up to 5 mol %) and/or DSPE-mPEG conjugates (wherein the molecular weight of PEG is typically within the range of 750-5000 daltons, e.g. 2000 daltons). The phospholipid composition of an exemplary PEGylated lipsome of the invention may comprise from about 1 mol % to about 20%, e.g., from about 1 mol % to about 5 mol % of PEG-lipid conjugates.

Furthermore, in certain embodiments, one or more moiety on the surface of the liposome specifically target the liposome to a particular cell type, tissue or the like. Targeting of liposomes using a variety of targeting moieties (e.g., ligands, receptors and monoclonal antibodies) has been previously described. Suitable examples of such targeting are known in the art. Targeting mechanisms generally require that the targeting agents be positioned on the surface of the liposome in such a manner that the target moieties are available for interaction with the target, for example, a cell surface receptor. In an exemplary embodiment, the liposome is manufactured to include a connector portion incorporated into the membrane at the time of forming the membrane. An exemplary connector portion has a lipophilic portion which is firmly embedded and anchored in the membrane. An exemplary connector portion also includes a hydrophilic portion which is chemically available on the aqueous surface of the liposome. The hydrophilic portion is selected so that it will be chemically suitable to form a stable chemical bond with the targeting agent, which is added later. Techniques for incorporating a targeting moiety in the liposomal membrane are generally known in the art.

Exemplary Formulation

In an exemplary embodiment, the invention provides a formulation of a liposome comprising a lipid component of the invention. The liposome include a second component is a member selected from distearoyl phosphatidylcholine (DSPC), 1,2-dipalmitoyl-sn-glycero-3-phosphocholine (DPPC), hydrogenated soy phosphatidylcholine (HSPC), cholesterol, 1,2-distearoyl-sn-glycero-3-phosphoethanolamine-mPEG (DSPE-mPEG) and a combination thereof.

An exemplary lipsosome of the invention: (i) about 1% to about 15% of a paramagnetic chelate lipid according to Formula I; (ii) about 50% to about 60% matrix lipid selected from distearoyl phosphatidylcholine (DSPC), 1,2-dipalmitoyl-sn-glycero-3-phosphocholine (DPPC), hydrogenated soy phosphatidylcholine (HSPC) and a combination thereof; (iii) about 10% to about 40% cholesterol; and (iv) about 1% to about 5% 2-distearoyl-sn-glycero-3-phosphoethanolamine-mPEG (DSPE-mPEG).

The liposome of the invention is selected from a lyophilized liposome and a formulation in which said liposomes are suspended in a pharmaceutically acceptable diluent.

In an exemplary embodiment, the invention provides a liposome formulation of the gadolinium macrocycle in which the macrocycle has an in vivo $T_{1/2}$ of from about 12 hours to about 48 hours, e.g., from about 18 hours to about 24 hours, in a subject to whom it is administered.

In an exemplary embodiment, the liposomes of the invention are from about 90 nm to about 140 nm in diameter.

Pharmaceutical Formulations of the Invention

For intravenous, cutaneous or subcutaneous injection, or injection at the site of affliction, the liposome of the invention will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

The paramagnetic chelate will be, in various embodiments, present in the liposome as a pharmaceutically acceptable salt. This refers to instances in which the chelating agent includes one or more negative charges not "neutralized" by the positive metal, e.g., Gd(III)-DOTA), the counterion is "pharmaceutically acceptable".

Methods of the Invention

The present invention also provides methods of imaging, or otherwise acquiring MR data, from a pregnant subject, because of non-toxicity to the fetus(es) of the contrast media of the invention, where other contrast agents have black box warning because of potential fetal toxicity. In various embodiments, the methods are of use as a diagnostic for placental conditions such as IUGR, Preeclampsia, and GDM. The invention also provides a similar method for a non-pregnant subject using a contrast medium of the invention.

Contrast agents of the invention also provide advantages in imaging of subjects who are not pregnant, lowering concerns about nephrogenic systemic fibrosis and brain deposition side effects of Gd-based contrast media. Accordingly the invention also provides methods of imaging subjects who are not pregnant.

An exemplary method of the invention includes administering to the subject a diagnostically effective amount of the agent of the invention and, thereafter, acquiring one or more MR datasets from the subject. The datasets are at least partially acquired from regions of interest (ROI) in the subject into which the contrast agent of the invention has been delivered. In an exemplary embodiment, the ROI includes the placenta. In various embodiments, the ROI includes the placenta and the fetus(es) and, from the dataset acquired, it is apparent that less than about 1%, 2%, 3%, 4%, 5%, 6%, 7%, 8%, 9% or less than about 10% of the dosage of the contrast agent administered to the pregnant subject has entered the vascular system of the fetus(es).

Elements of MR Image Formation

Certain atomic nuclei possess a non-zero spin, which gives rise to a net magnetic moment. The nuclear magnetic moments of water protons (hydrogen atoms) supply the signal in most MR imaging experiments. The sample to be imaged is placed in a strong static magnetic field that induces the sample to become slightly magnetized with a net magnetic moment in the direction of the applied field, with an energy (angular momentum) proportional to the applied field. To encode spatial information, other fields are applied as gradients along one or more orthogonal axes. Each position in space is uniquely encoded by the energy or phase of the spins there. A radio frequency field is pulsed through the sample and the energy absorbed results in a reorientation of the net nuclear magnetization in a new direction (typically a pulse is applied to tilt the magnetization 90 degrees). After this perturbation, net energy loss by a variety of processes returns the net magnetization to its initial equilibrium orientation. The formation of an image from this process has a complicated dependence on a large number of factors.

In a typical experiment, one modifies the imaging parameters to reduce the contributions from many of these factors. In the most typical MRI experiments, signal intensity is primarily derived from proton concentration and relaxation times. Relaxation times characterize the return of net magnetization to equilibrium. It is the difference in signal intensities between spatial regions that provides contrast. Proton concentration can vary by a large percentage between soft tissue and bone, providing sharp contrast. Differences in proton density between soft tissues is more subtle, however, and contrast more likely is derived from tissue-dependent differences in relaxation times, which depend strongly on local environment.

Contrast Enhancement

Though the invention is exemplified herein by reference to a Gd-based contrast agent, those of skill in the art will appreciate that the instant invention is not so limited and has broad applicability across a range of compounds imparting contrast to tissues in imaging experiments. The invention finds particular, but not sole, applicability as a component of a paramagnetic contrast medium for use in conjunction with MRI.

The need to differentiate tissues or organs that are magnetically similar but histologically distinct has been a major impetus for the development of contrast enhancement agents. They are called contrast agents because signal is increased in their presence, thus improving contrast between that tissue and surrounding tissues. More than 30% of all clinical MR exams now employ contrast agents. However, current clinical MRI agents are not sensitive to biochemical events in cells or organs—rather, being always active they enhance the signal wherever they are present. Distinguishing tissues relies on differential distribution of contrast agents between tissues, which does not always occur. Contrast agents that are responsive to microenvironmental differences between tissues allow discrimination based on biochemical events, extending the potential applications for MRI beyond simple anatomy.

Paramagnetic elements, such as lanthanides, make effective contrast agents. Unpaired electrons in the paramagnetic ions interact directly with surrounding water protons to dramatically reduce their relaxation times. This change in the relaxation times translates to enhanced signal. The effects of contrast agents are generally reported in terms of relaxation rates or relaxivity of the water protons, which are inversely related to the relaxation times and reflect the overall contributions of all relaxation mechanisms at work in the system. Water access to the paramagnetic ions is important for the effect (first sphere coordination).

The principles and practice of MRI image formation with and without contrast enhancement are well known to those of skill in the art and are discussed in greater detail in Aime, et al., *JMRI* 16:394-406 (2002); Caravan, et al., *Chem. Rev.* 99:2293-2352 (1999), and Gadian, NMR and its Applications to Living Systems, $2^{nd}$ Edition, Oxford Science Publications (1995), the entire disclosures of which are incorporated by reference in their entirety for all purposes.

Methods of the invention comprise administering a sufficient amount of a liposome of the invention in vivo or in vitro and obtaining one or more contrast-enhanced MRI images of the pregnant subject, or experimental system. Methods of the invention further comprise assaying the activity of compounds of the invention in in vivo or in vitro tests to characterize the compounds of the invention.

Methods for diagnosing, characterizing the severity of, and staging diseases that affecting pregnant subjects also are encompassed by the present invention. The methods of the invention include administering a diagnostically effective amount of the liposome of the invention to the subject and acquiring an image or images of the subject after the administration. The liposomes of the invention can be formulated in pharmaceutical formulations for in vivo administration to the pregnant subject. These formulations can comprise, in addition to one or more of the compounds of the invention, a pharmaceutically acceptable excipient, carrier, buffer, stabiliser or other materials well known to those skilled in the art. Such materials should be non-toxic and should not interfere with the function of the active compound. The precise nature of the carrier or other material can depend on the route of administration, e.g. oral, intravenous, cutaneous or subcutaneous, nasal, intramuscular, intraperitoneal routes.

The actual amount administered, and rate and time-course of administration, will depend on the nature of the compound, as well as the target area to be imaged. Prescription of the contrast agent, e.g. decisions on identity of contrast agent, dosage, etc., is within the ordinary skills of radiologists and other medical providers, and typically takes account of the disorder to be imaged, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

The following examples are provided to illustrate, but not limit, the invention.

EXAMPLES

Example 1

Materials and Methods
Liposomal Gd Contrast Agent

The liposomal Gd agent contrast agent was prepared as per procedures described previously. Briefly, 1,2-Dipalmitoyl-sn-glycero-3-phosphocholine (DPPC), Gd-DTPA bis (stearylamide) (Gd-DTPA-BSA), Cholesterol and 1,2-distearoyl-sn-glycero-3-phosphoethanolamine-N-[methoxy(-poly(ethylene glycol))-2000] (mPEG2000-DSPE) were dissolved in ethanol at a molar ratio 30:25:40:5. The ethanolic lipid solution was hydrated with 150 mM saline/10 mM histidine to achieve a lipid concentration of 75 mM. The solution was stirred for 30 minutes at 60 C and then sequentially extruded on a Lipex Thermoline extruder to size the liposomes to ~120 nm. The resulting solution was dialyzed against 150 mM saline/10 mM histidine. The mean liposome size in the final formulation, determined by dynamic light scattering (DLS), was ~120 nm. The gadolinium and phospholipid (equivalent phosphorus) concentration in the liposomal formulation, quantified using inductively coupled plasma optical emission spectroscopy (ICPOES), were 16 mM and 25 mM, respectively.

For in vivo studies, liposomal-Gd was administered intravenously via the tail vein at a dose of 0.2 mmol Gd/kg.

Animal Model

All animal studies were performed under a protocol approved by the Institutional Animal Care and Use Committee of the Baylor College of Medicine.

Fifteen pregnant Sprague Dawley rats (8-9 weeks old; ~175-199 g gram body weight before pregnancy) were used in the study. Conventional Gd contrast agent was used with six of these animals, and the liposomal-Gd was used with nine of the animals. The first day of gestation, designated as 0.5, was when a vaginal copulation plug was detected. Imaging was performed on day 18.5 of pregnancy.

Magnetic Resonance Imaging (MRI)

Imaging was performed on a 1 T permanent MRI scanner (M2 system, Aspect Technologies, Israel). A 60 mm volume coil was used for transmit and receive of RF signal.

Animals were sedated using 3% isoflurane, setup on the MRI animal bed and then maintained at 1-1.5% isoflurane delivered using a nose cone setup. The body temperature was maintained by circulating hot water in the MRI animal bed. Respiration rate was monitored using a pneumatically controlled pressure pad placed in the abdominal area underneath the animal.

In the study with the conventional Gd contrast agent, dynamic contrast enhanced MRI (DCE-MRI) was performed using gadoterate meglumine (Gd-DOTA, Dotarem®) to evaluate visualization of the retroplacental space. DCE-MRI was performed using a T1w 2D gradient echo sequence (GRE) sequence with the following scan parameters: TE=3.5 ms, TR=15 ms, FA=25, slice thickness=0.8 or 1.6 mm, NEX=12; temporal resolution=47 s. Four non-contrast, baseline images were acquired followed by bolus intravenous administration of gadoterate meglumine (0.15 mmol Gd/kg). Post-contrast imaging was continued for upto 20 minutes after administration of gadoterate meglumine. In order to directly compare image quality between the two contrast agents, liposomal-Gd contrast agent (0.15 mmol Gd/kg) was administered a minimum of three hours later, allowing clearance of gadoterate meglumine. Post-liposomal-Gd contrast images were acquired using the same DCE-MRI protocol.

In the study with liposomal-Gd, all nine animals underwent pre-contrast and post-contrast scans. T1 weighted scans were acquired using a 3D gradient echo sequence (GRE). Scans were acquired in axial and coronal plane. Scan parameters for the T1w-GRE sequence were: echo time (TE)=3.5 ms, repetition time (TR)=20 ms, flip angle=70, slice thickness=1.0 mm, field of view=64 mm, number of slices=32, matrix=180×180, in-plane resolution=356×356 $\mu m^2$, scan time ~2 min.

T2w scans were acquired in coronal plane using a fast spin echo (FSE) sequence. Scan parameters for the T2w-FSE scans were: echo time (TE)=80 ms, repetition time (TR)=7952 ms, slice thickness=1.5 mm, field of view=60 mm, number of slices=38, matrix=256×250, in-plane resolution=234×240 $\mu m^2$, number of excitation=2, scan time ~7 min.

A high-resolution T1w-GRE sequence was used for coronal acquisition in the post-contrast scan. The scan parameters were: echo time (TE)=4.2 ms, repetition time (TR)=20 ms, flip angle=50, slice thickness=0.8 mm, field of view=80 mm, number of slices=120, matrix=300×300, in-plane resolution=266×266 $\mu m^2$, scan time ~12 min.

Four individual scans were acquired for each scan protocol. The dicom images from the individual scans were averaged in Matlab to quantitatively and qualitatively compare image quality of single versus averaged scan. The individual scans were reviewed for motion artifacts prior to averaging.

Computed Tomography (CT) Imaging

Imaging was performed on a small animal micro-CT system (Siemens Inveon). Animals were sedated with 3% isoflurane, setup on the MRI animal bed and then maintained at 1-1.5% isoflurane delivered using a nose cone setup. Respiration rate was monitored using a pneumatically controlled pressure pad placed in the abdominal area underneath the animal.

Contrast-enhanced CT angiography was performed after administration of liposomal-iodinated blood pool contrast agent (550 mg I/kg). The liposomal-iodinated contrast agent exhibits similar pharmacokinetics as its MR counterpart and has extensively been used for rodent vascular imaging.

Elemental Analysis of Tissue Gd Concentration

Animals were euthanized at 3 days after administration of the contrast agent due to the long blood circulation life of liposomal-Gd ($t_{1/2}$~18 h) and to allow additional time for possible transport of Gd to the fetus. Two animals, that had undergone MRI and CT imaging, were euthanized at the end of the imaging. The animals were dissected, the placentae and fetuses removed and transferred individually into polycarbonate vials for storage at −80 C. Maternal blood samples were collected and centrifuged to harvest the plasma which was then stored at −80 C. The plasma, placentae and fetuses were processed and analyzed as described previously for measurement of Gd concentration using the inductively-coupled plasma mass spectrometry (ICP-MS). Five fetuses and five placentae were analyzed for each pregnant animal.

Image Analysis

Qualitative and quantitative analysis of images was performed in Osirix (version 5.8.5, 64-bit, Pixmeo, Bernex, Switzerland).

Review of Images

Pre-contrast and post-contrast scans were reviewed by a trained maternal-fetal radiologist (~10 years of experience). T1 weighted GRE and T2 weighted FSE images were included in the review. Single (best of four scans) and averaged T1w-GRE images were reviewed for visualization of placental margin, retroplacental space and intra-placental vessel (central canal). The same procedure was followed for the DCE-MRI images acquired using conventional GD contrast agent. Single (best of four scans) and averaged T2w-FSE images were reviewed for visualization of contrast between placental margins and amniotic fluid. The visibility of target features in T1w and T2w images were scored by the radiologist on a 3-point scale: 0=not visible, 1=partly visible and 2=clearly visible. Data were presented as average and standard deviation of the scores.

Quantitative Analysis

Signal to noise ratio (SNR) and contrast to noise ratio (CNR) were determined for single scan and averaged scans, in pre-contrast and post-contrast liposomal-Gd scans. T1w-GRE and T2w-FSE images were included in the analysis. SNR in T1w-GRE images was determined for the placenta, retroplacental space and amniotic fluid. CNR in T1w-GRE images was determined between placenta and retroplacental space and between placenta and amniotic fluid. SNR in T2w-FSE images was determined for the placenta and amniotic fluid. Retroplacental space was not visible in T2w-FSE images. CNR in T2w-FSE images was determined between placenta and amniotic fluid.

Determination of Placenta Fractional Blood Volume

The intravascular property of liposomal-Gd enables direction measurement of fractional blood volume. The concentration of liposomal-Gd determined using ICP-MS in maternal blood and placentae was used for determination of placenta FBV. Plasma Gd concentrations were converted to maternal Gd concentrations using a 37.1% hematocrit value for the pregnant animals. Placenta FBV was calculated as the ratio of liposomal-Gd in maternal blood to the liposomal-Gd in the placentae.

Placenta FBV was also determined from MRI and CT datasets. The placentae were manually segmented in MRI and CT images. At least ten placentae were segmented per animal. The volume of segmented placenta and the average signal intensity were determined for each placentae. Region of interests were drawn in the inferior vena cava on three different images for determining the average signal intensity in the blood. MRI-derived FBV was computed as the ratio of average signal intensity in placental volume to the average signal intensity in maternal blood. Similarly, placental volume, average placental and maternal blood signal intensity were determined in CT images.

Statistical Analysis

The Wilcoxon rank sum test was used for statistical analysis of SNR and CNR values in pre-contrast and post-contrast images. The Chi squared test was used for statistical analysis of the radiologist scores. P-values<0.05 were considered to indicated a statistically significant difference. The Pearson's coefficient was computed when comparing parameter values (placental volume and placental fractional blood volume) determined using two different methods.

Results

Figure 7:
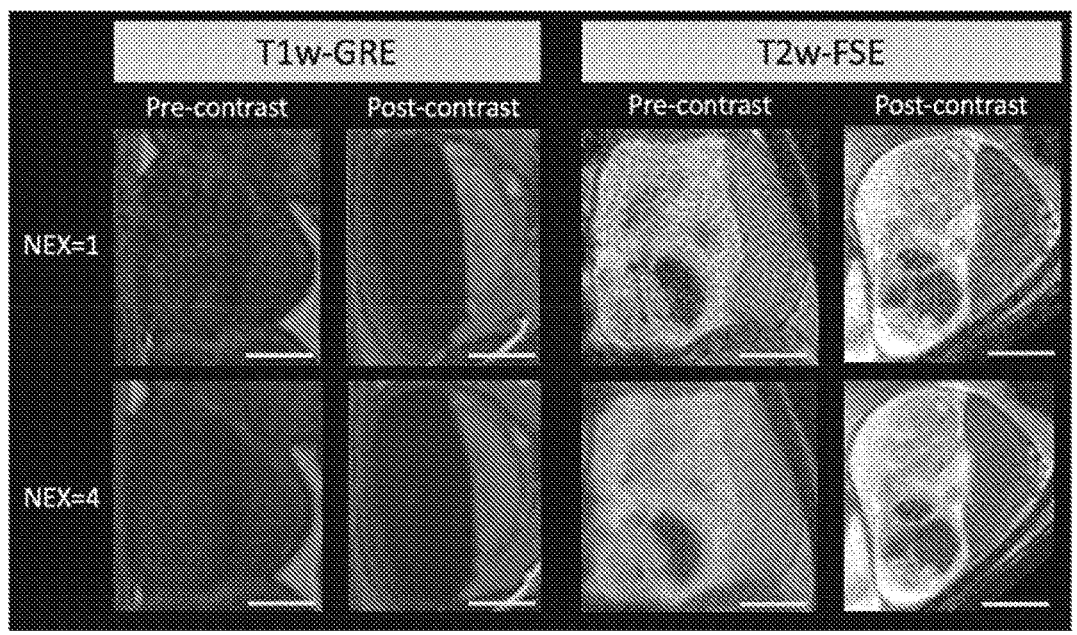
FIG. 7. Liposomal-Gd caused signal intensity changes in post-contrast T1-weighted and T2-weighted images. In T1w-GRE images, signal enhancement due to T1 shortening was seen in the placenta.

Liposomal-Gd caused signal intensity changes in post-contrast T1-weighted and T2-weighted images (FIG. 7). In T1w-GRE images, signal enhancement due to T1 shortening was seen in the placenta. Signal enhancement was uniform throughout the placenta since post-contrast images were acquired several minutes after administration of liposomal-Gd, by which time the agent is uniformly distributed in the maternal circulatory system. In T2w-FSE images, signal decrease due to T2 shortening was seen in the placenta. Similar to T1w images, the change in signal intensity was uniform throughout the placenta in T2w images. The retroplacental space was clearly visible in the post-contrast T1w images. The multi-scan averaged images improved visualization of features due to reduction in noise levels.

Figure 21:
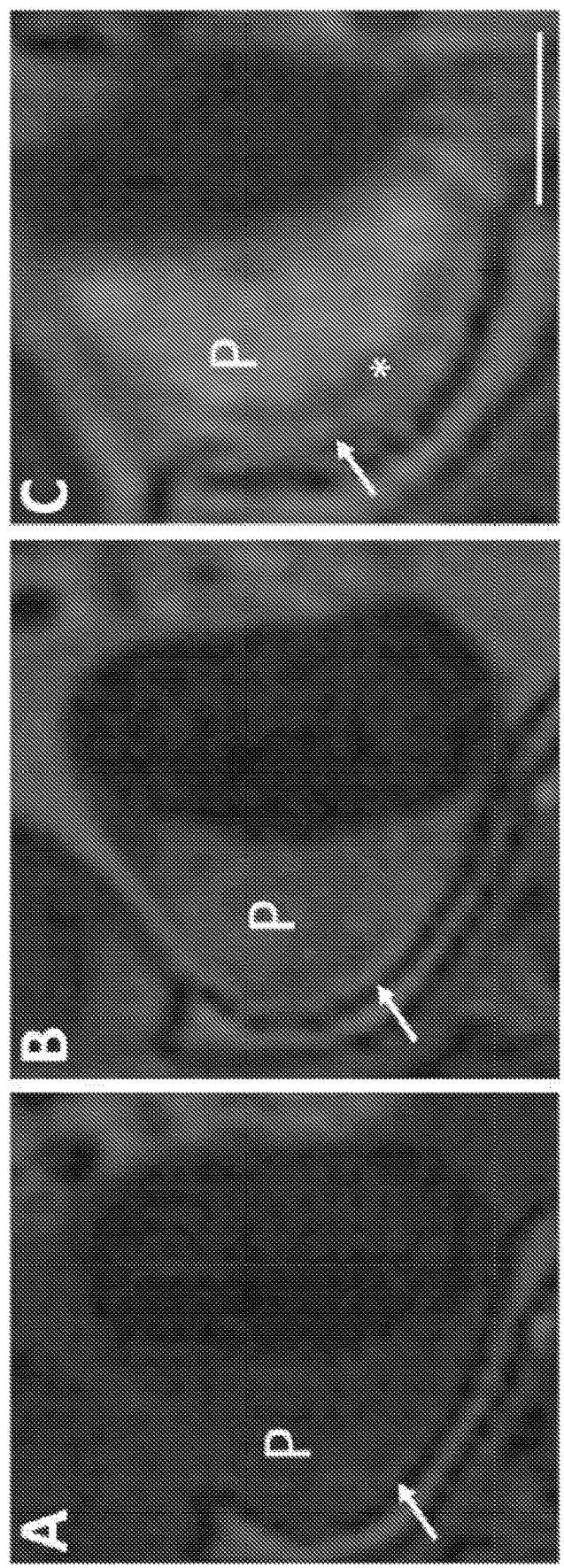
FIGS. 21A-C. MR imaging of retroplacental space. DCE-MRI image showing the placenta (P) and the myometrium wall (arrow) on (A) non-contrast image, (B) post-contrast image at peak enhancement obtained with clinically approved conventional contrast agent, gadoterate meglumine, and (C) post-contrast image acquired with liposomal-Gd. Note that the retroplacental space (*) is only visible on the liposomal-Gd enhanced image.

Multiphase dynamic contrast-enhanced MRI images using the conventional Gd agent demonstrated retrograde opacification of the placenta towards the myometrium. However, no consistent and reproducible visualization of the retroplacental space was demonstrated in the images acquired with the conventional contrast agent over the 20 minute post-contrast acquisition period (FIG. 21). The liposomal-Gd blood pool contrast agent demonstrated clear visualization of the placenta. More importantly, the blood pool agent enabled visualization of the retroplacental space (FIG. 21).

The high CNR values in post-contrast images translated into improved visualization of target features (FIG. 10). On T1w images, the placental margins were significantly better visualized (p<0.001) on post-contrast images (conventional Gd and liposomal-Gd) compared to pre-contrast images. Due to the high SNR values on post-contrast images, placental margins were clearly visible on both single acquisition and averaged acquisition liposomal-Gd images. The retroplacental space was only visible on the post-contrast T1w images acquired with liposomal-Gd. The visibility scores for retroplacental space on single acquisition and averaged acquisition liposomal-Gd images were not significantly different (p=0.38). The high SNR in the vessels enabled visualization of the central canal on the post-contrast T1w liposomal-Gd images. The visibility scores for central canal, which was only seen on post-contrast liposomal-Gd images, in single acquisition and averaged acquisition images were not significantly different (p=0.28). On T2w images, the contrast between the placental margin and amniotic fluid compartment was higher in post-contrast liposomal-Gd images compared to pre-contrast images (Table 1-2). The single acquisition images and averaged acquisition post-contrast T2w liposomal-Gd images were rated equivalent for placental margin delineation.

Figure 8A:
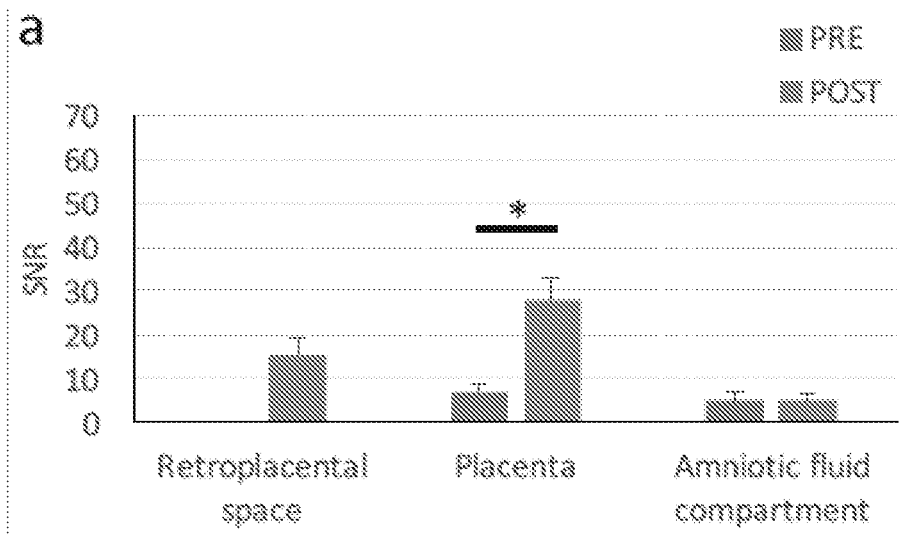
FIG. 8A. Quantitative image analysis of T1w-GRE scans demonstrated a significantly higher (p<0.05) signal-to-noise ratio (SNR) within the placenta in post-contrast images (right bar in each pair) compared to pre-contrast images (left bar in each pair). No significant differences in SNR were observed within the amniotic fluid compartment in pre-contrast and post-contrast images. Nex=1
Figure 8B:
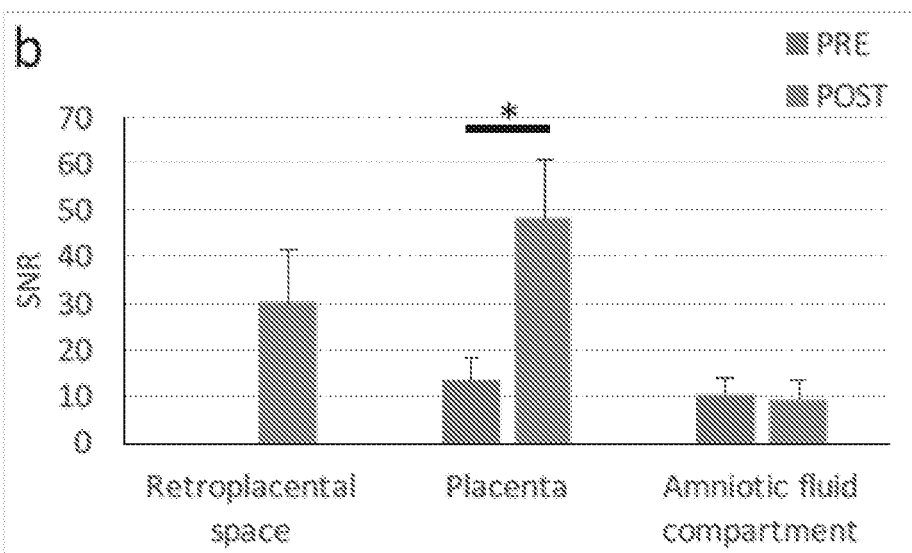
FIG. 8B Quantitative image analysis of T1w-GRE scans demonstrated a significantly higher (p<0.05) signal-to-noise ratio (SNR) within the placenta in post-contrast images (right bar in each pair) compared to pre-contrast images (left bar in each pair). No significant differences in SNR were observed within the amniotic fluid compartment in pre-contrast and post-contrast images. Nex=4
Figure 8C:
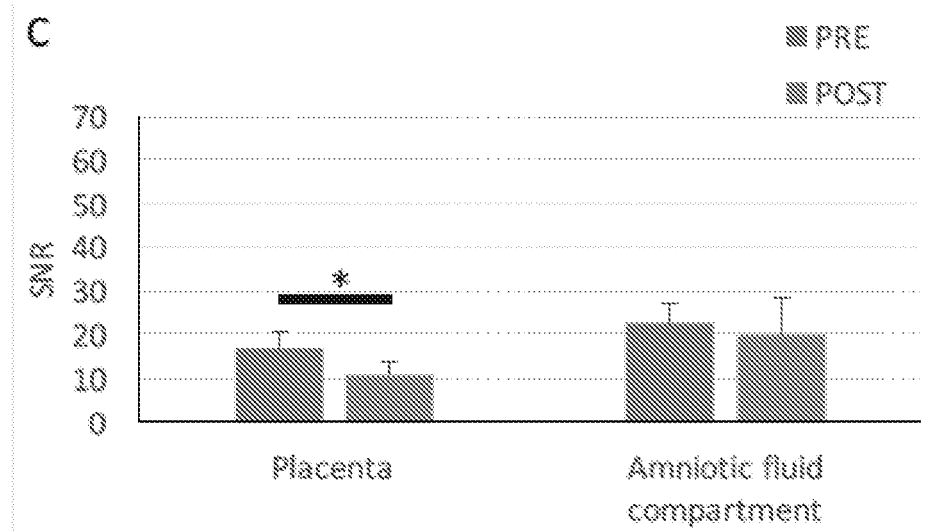
FIG. 8C Quantitative image analysis of T2w-FSE scans demonstrated a significantly higher (p<0.05) signal-to-noise ratio (SNR) within the placenta in pre-contrast images (left bar in each pair) compared to post-contrast images (right bar in each pair). No significant differences in SNR were observed within the amniotic fluid compartment in pre-contrast and post-contrast images. The retroplacental space is not distinguishable in the T2w images. NEX=1
Figure 8D:
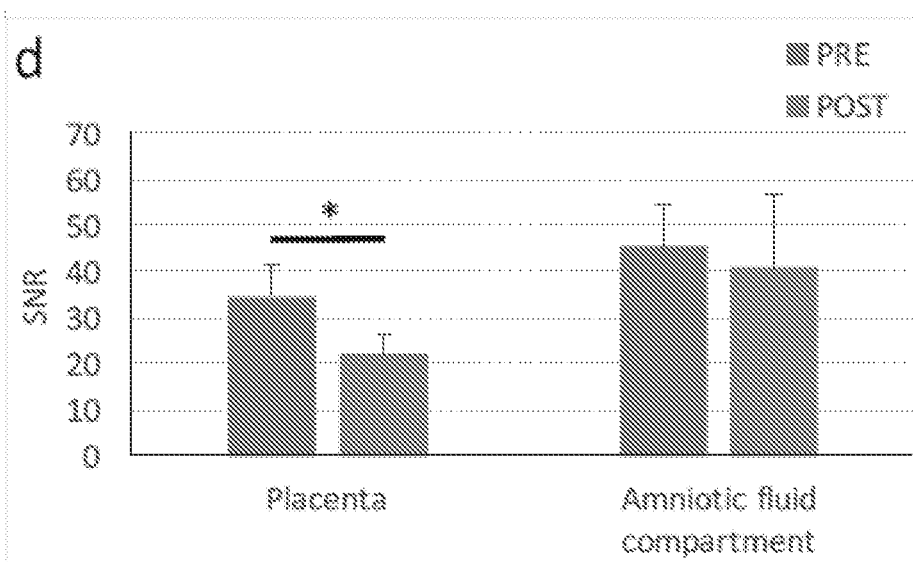
FIG. 8D. Quantitative image analysis of T2w-FSE scans demonstrated a significantly higher (p<0.05) signal-to-noise ratio (SNR) within the placenta in pre-contrast images (left bar in each pair) compared to post-contrast images (right bar in each pair). No significant differences in SNR were observed within the amniotic fluid compartment in pre-contrast and post-contrast images. The retroplacental space is not distinguishable in the T2w images. NEX=4
Figure 9A:
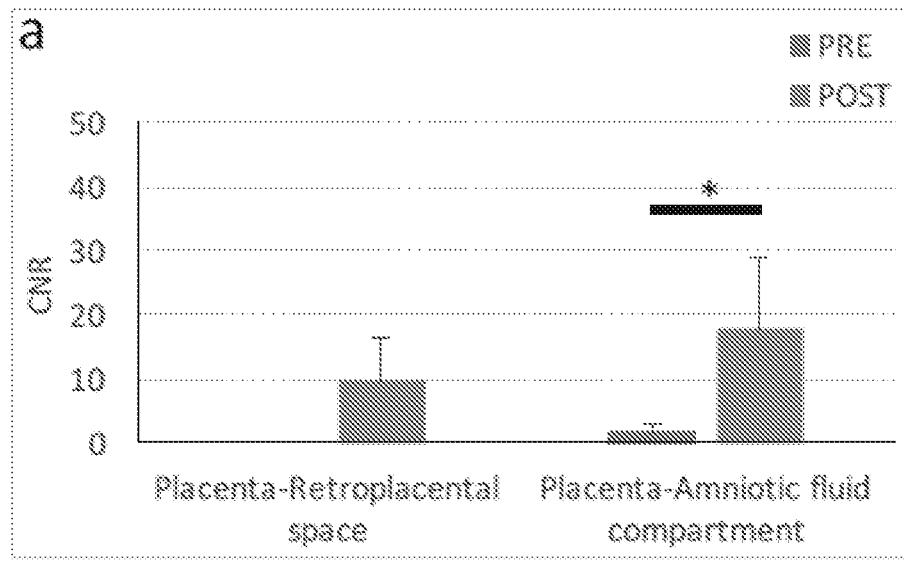
FIG. 9A. Same data as in FIG. 8A, plotted as a Contrast to Noise Ratio. Contrast is defined as the difference in signal between the regions specified in the category axis.
Figure 9B:
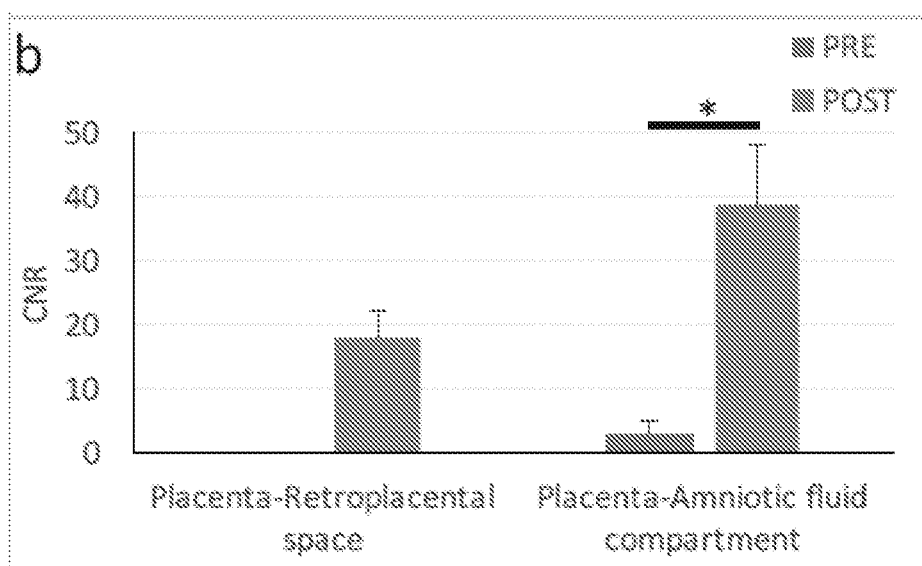
FIG. 9B. Same data as in FIG. 8B, plotted as a Contrast to Noise Ratio. Contrast is defined as the difference in signal between the regions specified in the category axis.
Figure 9C:
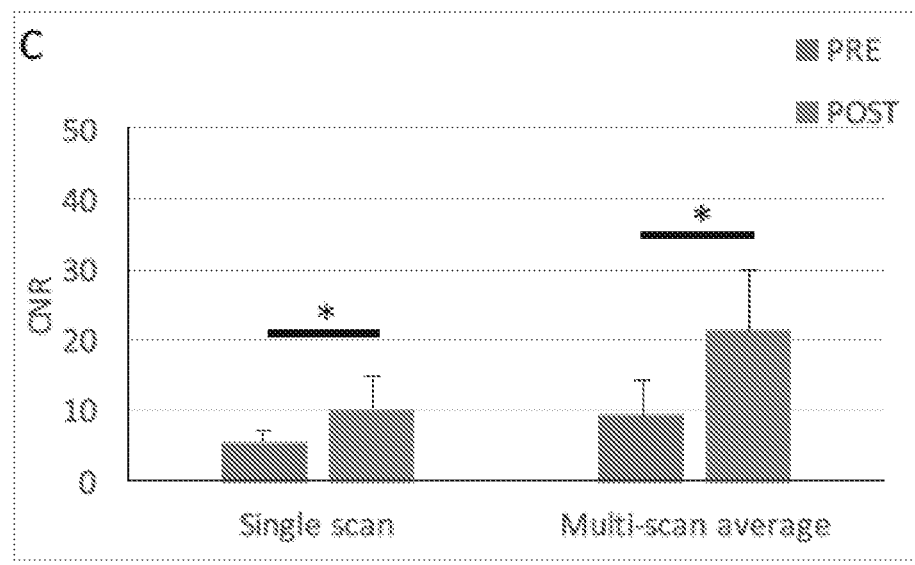
FIG. 9C. Data for CNR between the placenta and the amniotic fluid from FIG. 8C and FIG. 8D, single scan is NEX=1, Multiscan average is NEX=4. The retroplacental space is not visualized in T2w images.
Figure 10A:
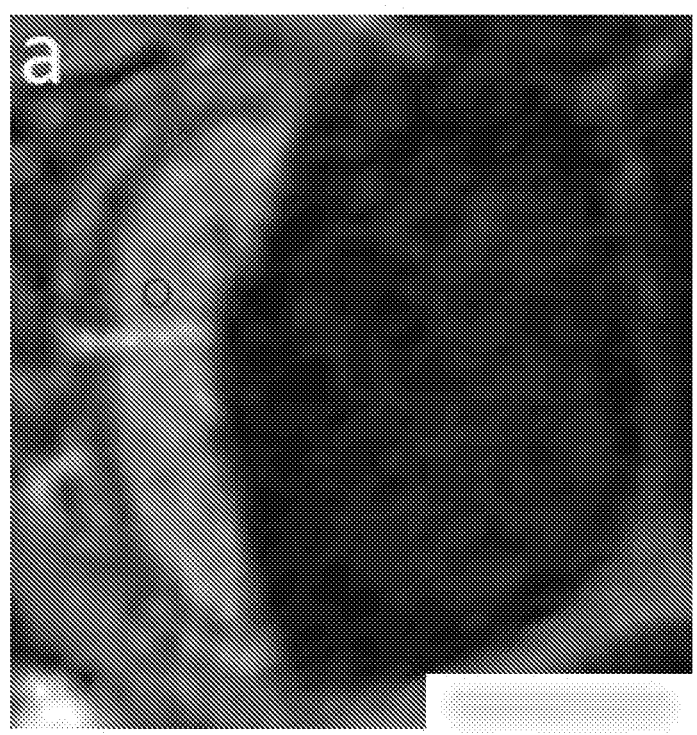
FIGS. 10A-F. Visualization of placental features in liposomal-Gd enhanced MRI and liposomal-iodine enhanced CT images. Orthogonal 3-plane view of the placenta in a pregnant rat on liposomal-Gd post-contrast T1-weighted MR images (A, B, C) and liposomal-iodine enhanced CT images (D, E, F) demonstrating visualization of retroplacental space (*) and central canal (circle). Scale bar represents 5 mm. The high CNR values in post-contrast images translated into improved visualization of target features. In T1w images, the placental margins were better visualized in post-contrast images compared to pre-contrast images.
Figure 10B:
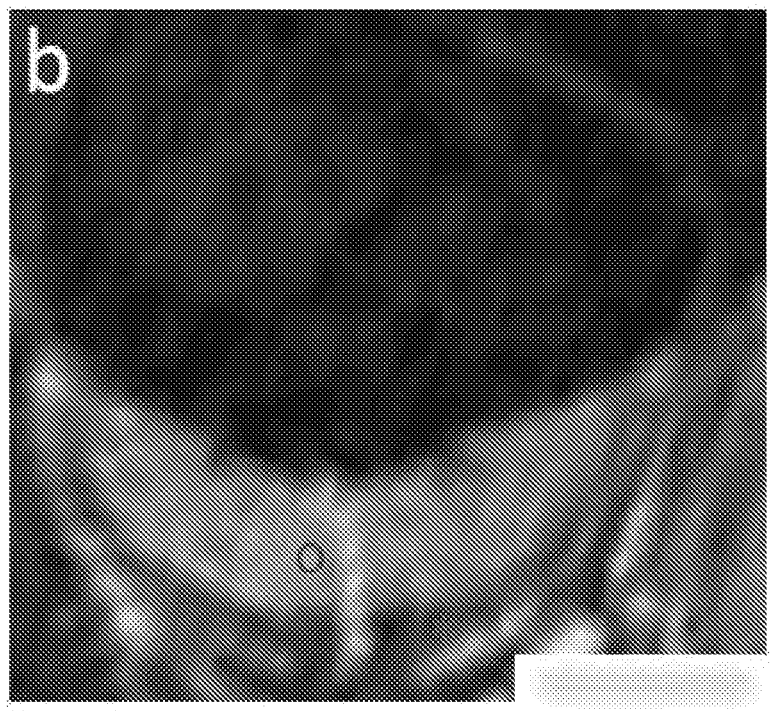
Figure 10C:
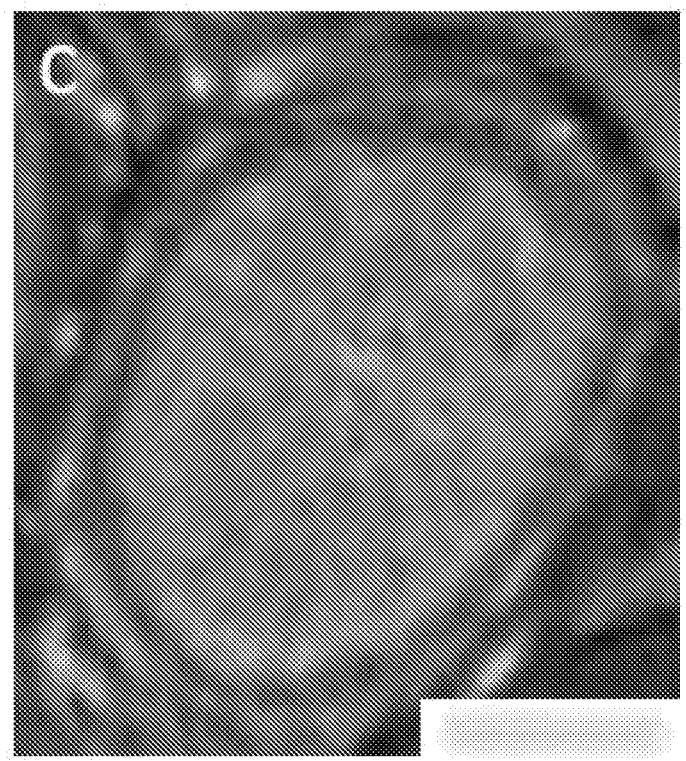
Figure 10D:
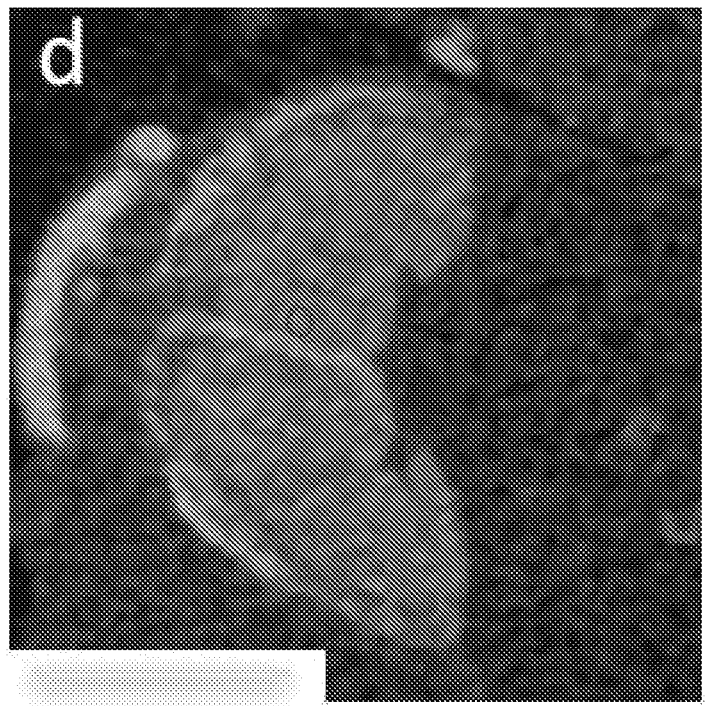
Figure 10E:
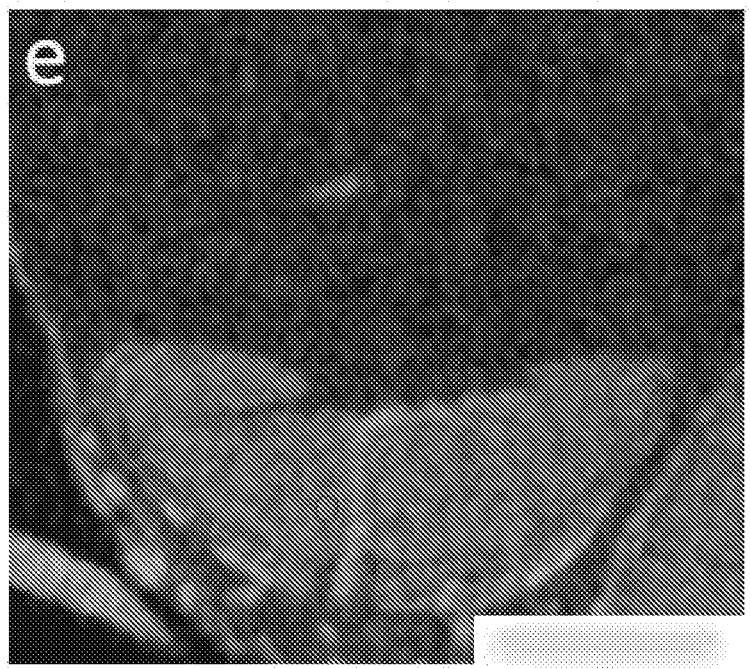
Figure 10F:
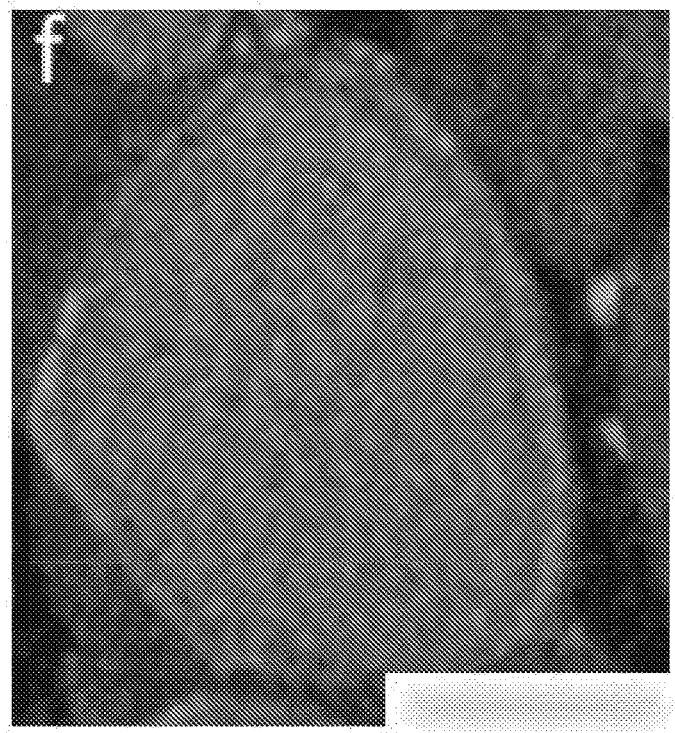

Quantitative image analysis of T1w-GRE scans acquired with liposomal-Gd demonstrated a significantly higher (p<0.05) signal-to-noise ratio (SNR) within the placenta in post-contrast images (28.0±4.7) compared to pre-contrast images (6.9±1.8) (FIG. 8A). No significant differences in SNR were observed within the amniotic fluid compartment in pre-contrast and post-contrast images. The retroplacental space was clearly demarcated in the post-contrast images and therefore allowed for determination of SNR. In the multi-scan averaged images, the SNR values increased about 2-fold compared to individual scans. The high values of SNR in the post-contrast images translated into improved CNR between the placenta and retroplacental space (9.7±6.6) and between the placenta and amniotic fluid compartment (18.0±10.7).

In T2w-FSE scans, a significant drop in SNR was seen within the placenta in post-contrast images (17.1±3.7) compared to pre-contrast images (10.9±2.8) (FIGS. 8 C and D). No significant differences in SNR were observed in the amniotic fluid compartment in pre-contrast and post-contrast T2w images. Similar to T1w images, an ~2-fold increase in SNR was obtained in the multi-scan averaged images compared to the single scan images. CNR between the placenta and the amniotic fluid compartment was significantly higher in post-contrast images (10.3±4.6) compared to pre-contrast images (5.7±1.4). The CNR values increased ~2-fold in the multi-scan averaged images for both the pre-contrast (9.4±4.7) and post-contrast images (21.5±8.3).

Figure 22:
FIG. 22. Volume-rendered 3D imaging of utero-placental vasculature in a pregnant rat on MRI and CT imaging. Coronal volume-rendered image demonstrating the placenta and associated utero-placental blood vessels in (left) contrast-enhanced MRI and (right) contrast-enhanced CT imaging. The retroplacental space, visible as a hypo-enhancing rim surrounding the placenta, is seen in the contrast-enhanced MRI volume rendered image (arrows).

The uniform opacification with liposomal-Gd enabled the acquisition of high-resolution 3D images of the placenta. High-resolution MR imaging (0.035 mm$^3$ voxel) clearly demonstrated placental features that were also visible on high-resolution CT angiography (0.00034 mm$^3$ voxel), including the retroplacental space and the central canal (FIG. 10). Pixelation seen in the MRI images is due to the magnification of the images and the use of multi-planar reconstruction of non-isotropic voxels. The uniform opacification of the maternal vasculature and placenta facilitated 3D visualization of the utero-placental vasculature (FIG. 22).

Figure 14:
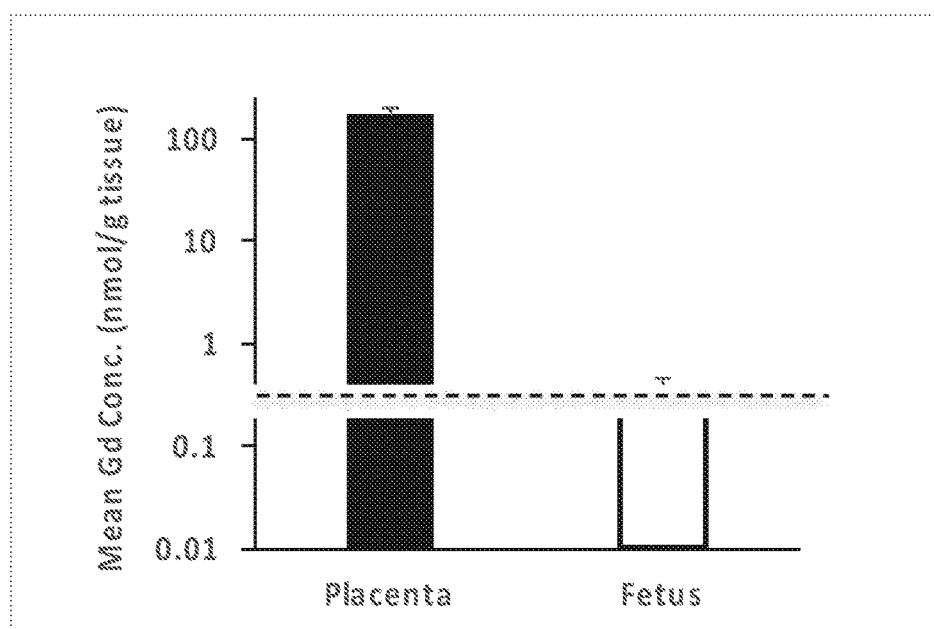
FIG. 14. ICP-MS analysis of gadolinium concentration in placentae and fetuses for animals injected with liposomal-Gd. Gd analysis was performed 72 hours post-injection of liposomal-Gd. The dotted line represents the 0.318 nmol/g tissue detection limit of ICP-MS. For each animal, five placentae and five fetuses were included in the analysis. 7 animals were included in the analysis. The error bars represent the standard deviations of the mean.

Elemental analysis for gadolinium in maternal blood and fetal units at 72 hours post-administration of liposomal-Gd demonstrated that the mean fetal Gd concentration was below the detection limit (dotted horizontal line on graph), and approximately 500-fold lower than the maternal blood Gd concentration (FIG. 14).

Figure 11:
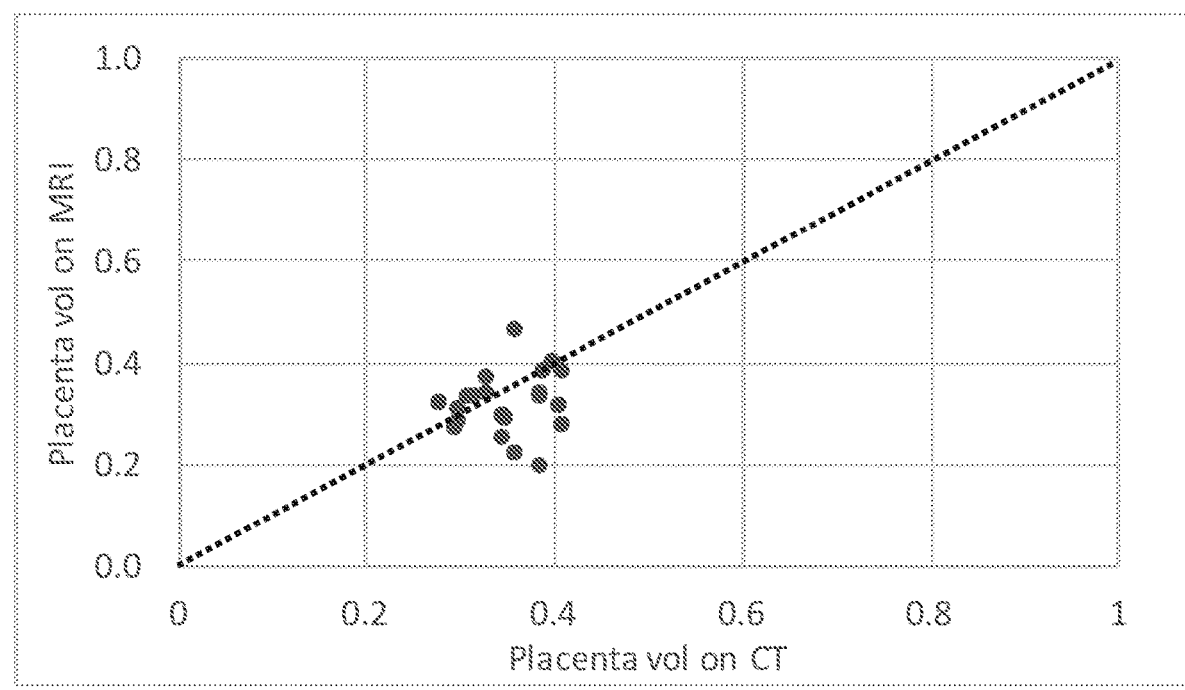
FIG. 11. Comparison of placental volume (cm$^3$) determined on MRI and CT images. A total of 20 placentae were segmented on MRI and CT images and included in the analysis.
Figure 12:
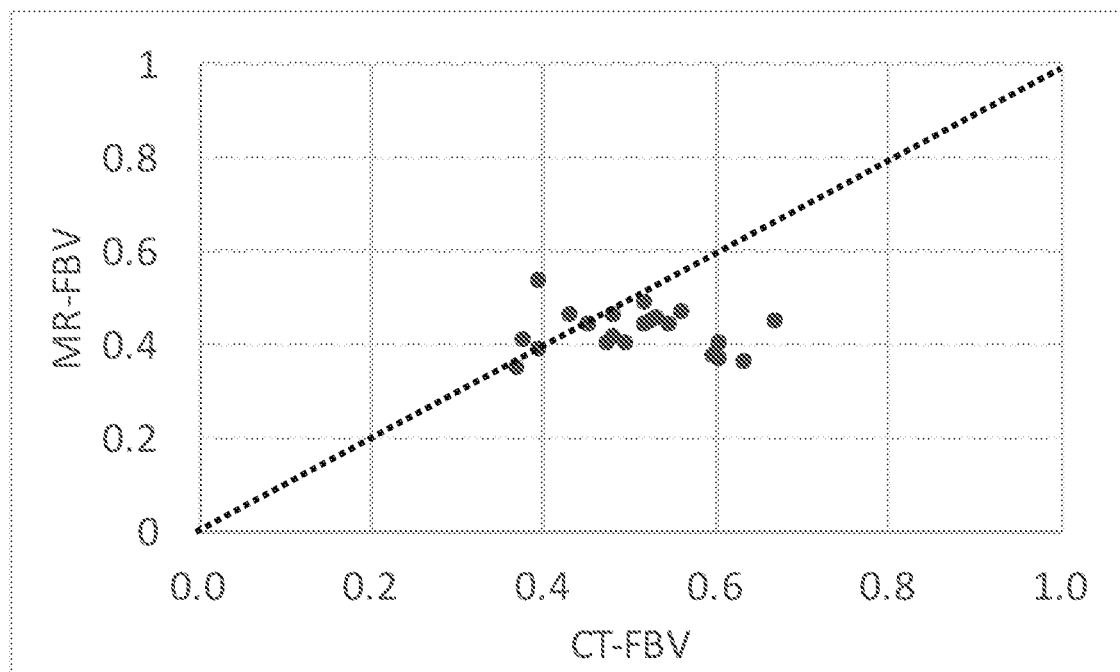
FIG. 12. Comparison of MRI derived and CT derived placental fractional blood volume (FBV). Each point represents individual placenta. A total of 20 placentae were included in the analysis.
Figure 13:
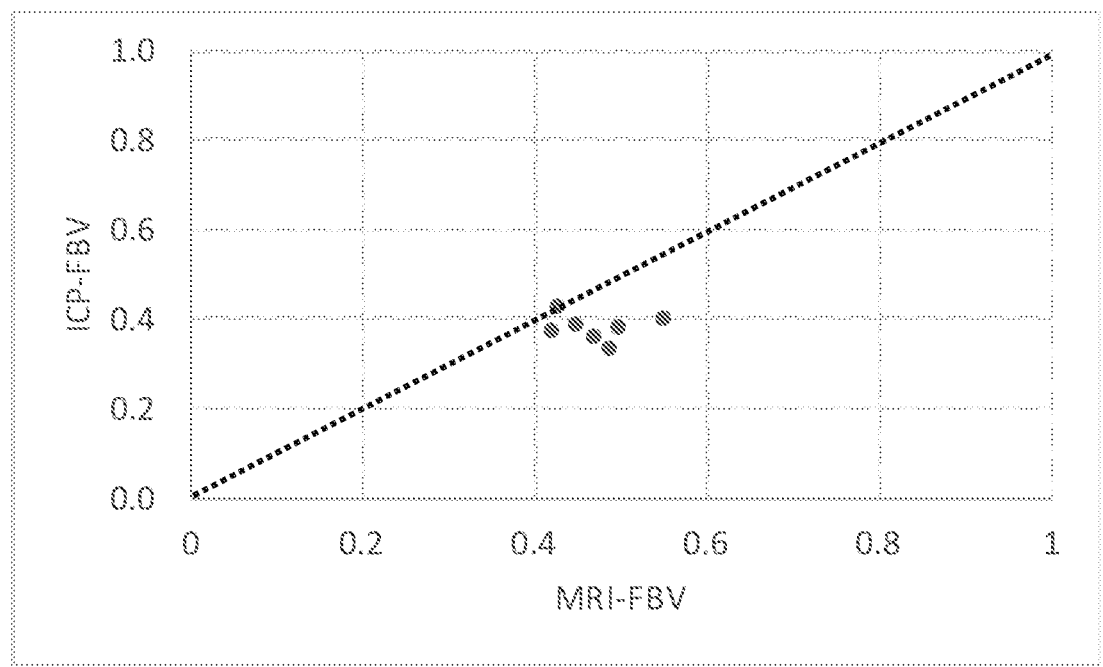
FIG. 13. Comparison of MRI derived and ICP-MS gadolinium assay derived placental fractional blood volume. Each point represents the mean FBV value of a pregnant animal. For each animal, 10 placentae were included in the MRI-FBV analysis and 5 placentae were included in the ICP-FBV analysis.

The uniform signal enhancement in the placenta facilitated segmentation and computation of placental volume on MR images (FIG. 11). Placental volumes were also determined on high-resolution CT images (35 um isotropic spatial resolution). The placental volumes determined on MRI and CT were clustered around the 45 degree line, demonstrating a good correlation between measurements performed on the two imaging modalities.

The intravascular nature of Liposomal-Gd facilitated determination of placental fractional blood volume (FBV). Placental FBV values were determined on a per placental basis for pregnant animals that were underwent MRI and CT imaging. MRI derived FBV and CT derived FBV values were clustered around the 45 degree line, demonstrating good correlation between measurements performed on the two imaging modalities (FIG. 11). MRI-derived FBV values were then compared with Gd elemental analysis (ICP-MS) derived FBV values on an animal basis.

Tables

TABLE 1-1

Visualization of placental features on T1-weighted GRE scans in pre-contrast and Liposomal-Gd contrast enhanced images. Visibility of features were scored by a fetal radiologist on a scale of 0-2 with 0 assigned to not visible, 1 assigned to partly visible and 2 assigned to clearly visible. Scores are reported as average and standard deviations. Images were acquired using a T1w-GRE sequence.

| | Non-contrast | | Liposomal-Gd enhanced | |
|---|---|---|---|---|
| Region of interest | NEX = 1 | NEX = 4 | NEX = 1 | NEX = 4 |
| Placental Margins | 1 | 1 | 2 | 2 |
| Retro-placental space | 0 | 0 | 1.3 ± 0.5 | 1.6 ± 0.5 |
| Central Canal | 0 | 0 | 1.6 ± 0.5 | 1.8 ± 0.4 |

TABLE 1-2

Visualization of contrast between placental margin and amniotic fluid compartment on T2-weighted scans in pre-contrast and Liposomal-Gd contrast enhanced images. Visibility of features was scored by a fetal radiologist on a scale of 0-2 with 0 assigned to not visible, 1 assigned to partly visible and 2 assigned to clearly visible. Scores are reported as average values and standard deviations. Images were acquired using a T2w-FSE sequence.

| | Non-contrast | | Liposomal-Gd enhanced | |
|---|---|---|---|---|
| Region of interest | NEX = 1 | NEX = 4 | NEX = 1 | NEX = 4 |
| Placental - amniotic fluid contrast | 1 | 1 | 2 | 2 |

Example 2

Contrast enhanced MRI is well suited to the assessment of both structure and perfusion dynamics, thus permitting detailed characterization of tissues and vascular structures. However, the use of contrast agents in human gravidae is discouraged because the placental-fetal membrane is permeable to most contrast agents, engendering potential exposure of the fetus. The technique has been demonstrated in animal models We tested two agents. (1) Gadobenate dimeglumine (Multihance®), a clinically used Gadolinium chelate, with a relatively short circulation half life and practically complete renal excretion. Like many Gd chelates, this agent does not significantly bind serum proteins, has a finite permeability through vascular endothelium, and its distribution volume is roughly equal to total extracellular water. Gadolinium induced toxicity primarily results from the dissociation of free Gd from the chelate, and to a relatively small extent from renal toxicity of intact chelate. Gadobenate is among the most stable chelates, and has been shown to release no more free Gd in native human serum than the two other well known low risk agents gadofosveset trisodium (Ablavar®) and gadopentetate dimeglumine (Magnevist®). However, of these three agents, the two linear chelates gadobenate and gadopentetate have relatively low albumin binding. Human serum albumin has significant permeability through the placental membrane and could therefore transport Gd across the barrier if it were to bind the Gd chelate. We therefore chose gadobenate dimeglumine as the conventional agent to test. (2) A novel liposomal contrast agent, encapsulating gadobenate dimeglumine in the interior, and incorporating a lipid-Gd-Chelate conjugate in the bilayer. Due to their large size (100-150 nm diameter, molecular weight $\sim 2\times 10^5$ kD), lipsomes exhibit very limited diffusion through intact vascular endothelium The liposome based Gd agents used in this study remain in the blood pool with a half-life of 18 to 24 hours. They are eliminated from blood by the reticuloendothelial system and cleared by the liver and spleen We hypothesized that nanoparticle based contrast agents would: (1) exhibit reduced permeation of the placental barrier compared to conventional agents, (2) demonstrate placental anatomy at least as well as conventional agents without toxicity to fetus.

The trans-placental permeability of liposomal gadolinium (Gd) nanoparticle contrast agents was evaluated in a pregnant mouse model. Pregnant Balb/c mice at 16.5 (±1) days of gestation were imaged using a 3D Spoiled Gradient Echo method at 9.4 T using two contrast agents: a clinically approved Gd chelate, Multihance® (gadobenate dimeglumine), and a novel experimental liposomal Gd agent. A Dynamic Contrast Enhancement (DCE) protocol was used to capture the dynamics of contrast entry and distribution in the placenta, and clearance from circulation. A blinded clinical radiologist evaluated both sets of images. A reference region model was used to measure the placental flow and physiological parameters; volume transfer constant (Ktrans), efflux rate constant (Kep). The Gd content of excised placentae and fetuses was measured, using inductively coupled plasma mass spectrometry (ICP-MS). MRI images of pregnant mice and ICP-MS analyses of placental and fetal tissue demonstrated undetectably low transplacental permeation of the liposomal Gd agent, while the clinical agent (Multihance) avidly permeated the placental barrier. Image interpretation and diagnostic quality was equivalent between the two contrast agents.

Results:

Mouse DCE-MRI Studies

The measured relaxivity (r1) of Multihance® was 3.99±0.52 and liposome Gd was 2.50±0.29 (sec·mM)$^{-1}$ at 9.4 T. In vivo, the pre-contrast relaxation time ($T_1(0)$) ranged from 800-1100 ms. The number of placentae visible varied from 2 to 5 per animal. The fetal-placental sac, placenta and fetus were distinguishable on $T_1$-weighted post-contrast images. The maternal artery and fetal left ventricle were not visible either due to restricted field-of-view (FOV) or from motion related blurring. Of the 25 mice tested, 14 mice received Multihance® and the images yielded 52 analyzable placentae. 9 mice received liposomal Gd and the images yielded 36 analyzable placentae. 2 mice received saline placebo and the images yielded 4 analyzable placentae.

Figure 15:
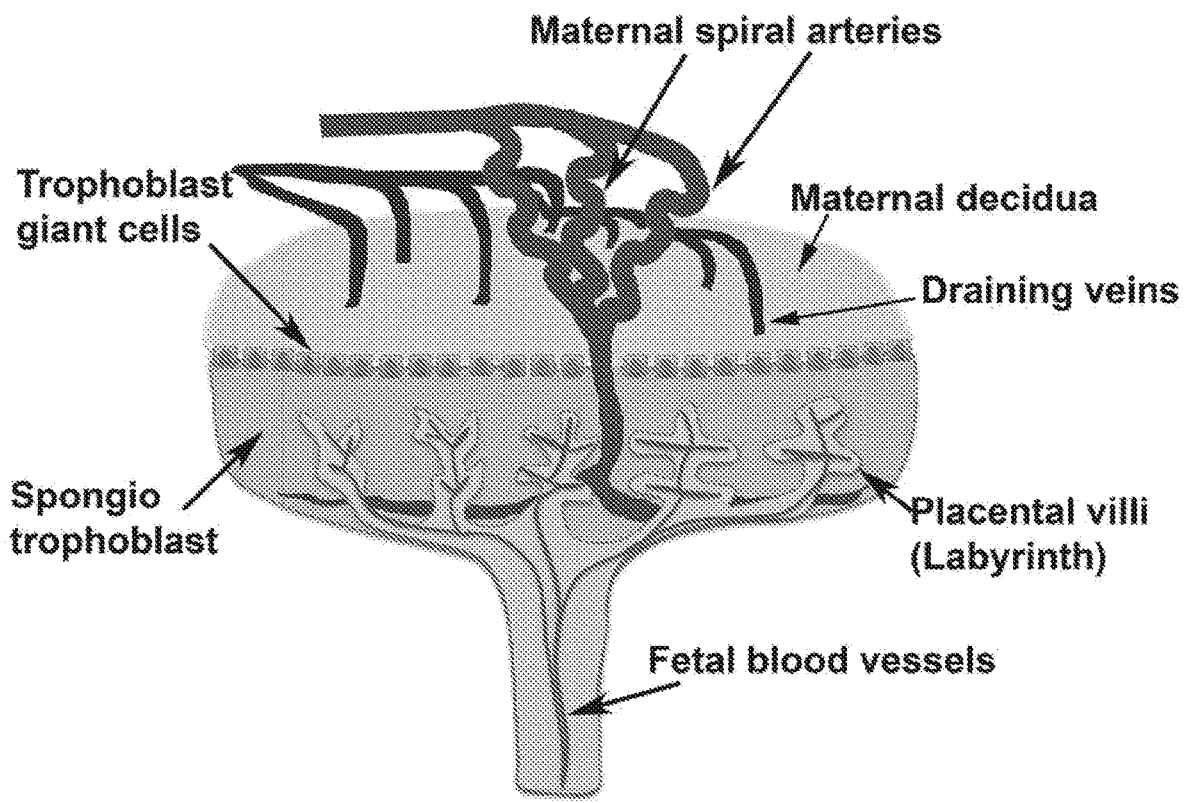
FIG. 15. Structure of the mouse placenta. The mature placenta (E14.5) consists of three layers: the labyrinth, the spongiotrophoblast, and the maternal decidua. The inner compartment of the hemochorionic placenta—the labyrinth—contains the villi where nutrients pass from the maternal blood into the foetal blood.

FIG. 15 shows a diagram of the placental circulation, and the locations of the labyrinth and decidual zones, as used in this analysis. The union of the labyrinth zone and the decidual zone was considered to be the entire placenta. In a typical DCE-MRI using gadobenate dimeglumine contrast, placentae can be seen enhanced by contrast, as the bolus moves into them. The labyrinth zone receives the contrast agent first, followed by a gradual filling of the rest of the placenta, further followed by a gradual decay in intensity as the agent is cleared from the maternal circulation. At the same time, a slight increase in intensity in the fetal sac is seen, as the agent filters into the fetal compartment.

Figure 16:
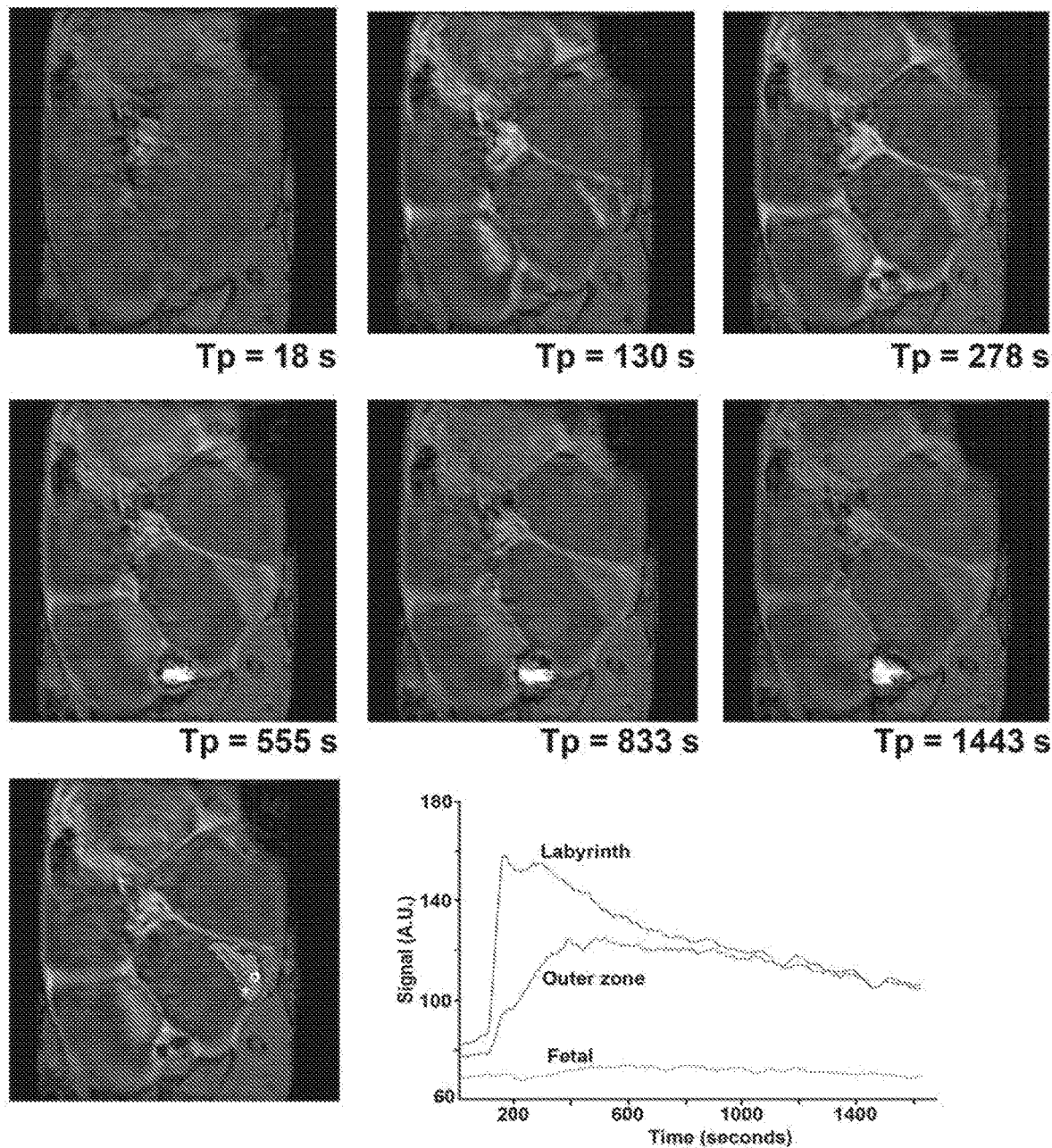
FIG. 16. Dynamic signal enhancement during the entry of conventional contrast agent (Multihance®:gadobenate dimeglumine) into the placenta. At 130 seconds, an artery carrying maternal blood to the placenta, the central arterial canal, and placental labyrinth are all enhanced. At subsequent points, the details of placental vasculature are obscured by enhancement of the peripheral placenta. The placental labyrinth shows early enhancement (asterisk) followed by the periphery (circle). Both zones then fade as the contrast is cleared from circulation. The transient signal in the two enhancing zones is shown in the graph.
Figure 17:
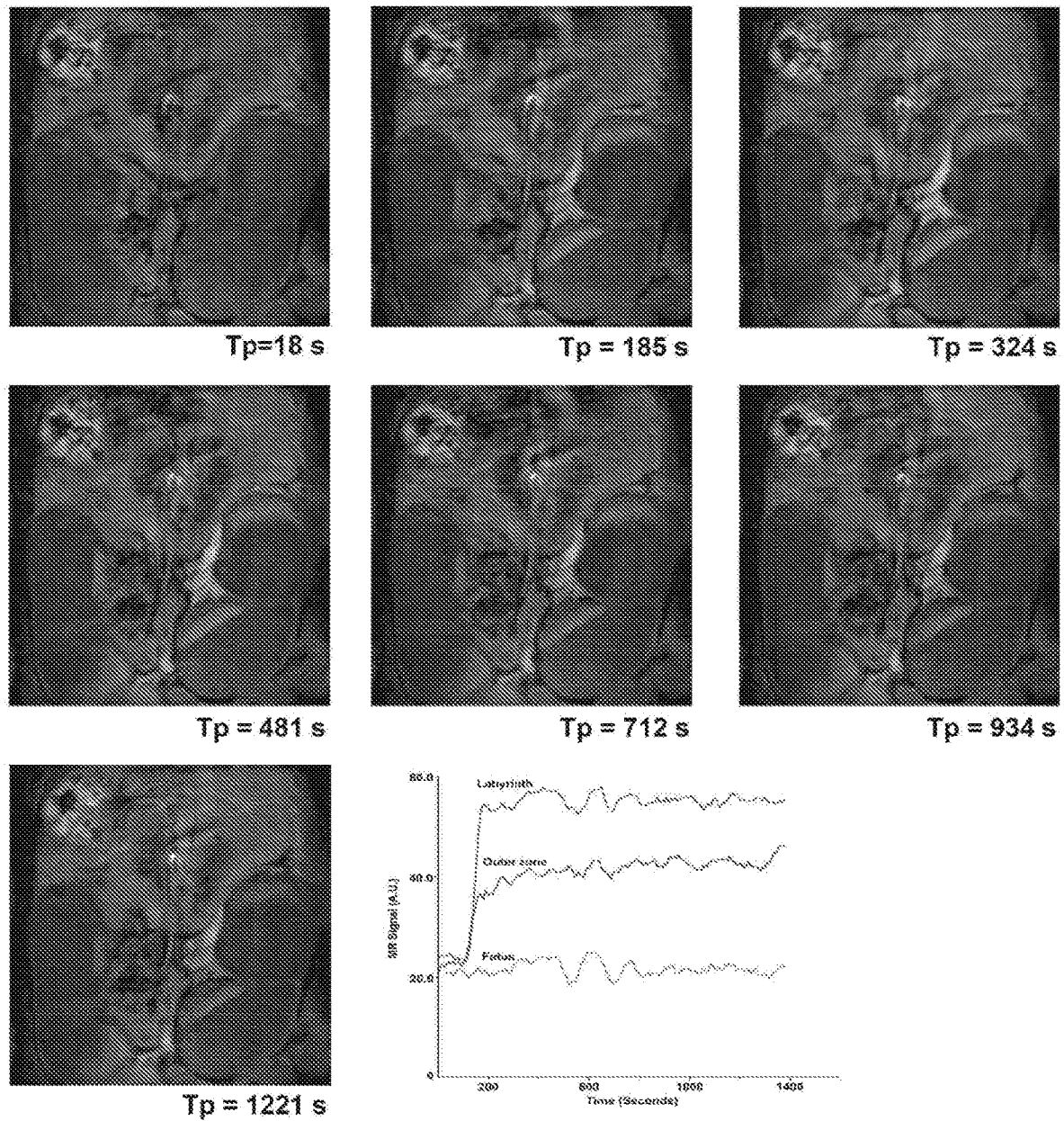
FIG. 17. Dynamic signal enhancement during the entry of liposomal contrast into the placenta. At 18 seconds, pre contrast entry, there is no enhancement visible. At 185 seconds, vessels entering the placenta, the labyrinth and periphery, are all enhanced. As the enhancement slowly fades, the labyrinth appears to retain contrast even at the last time point collected (1221 seconds, ~20 minutes post injection).

The signal enhancement at progressive time points, as a result of contrast agent circulation is shown in FIG. 16. The central arterial canal feeding in to the placental labyrinth is visible at the 130 s time point. Within each placenta, two zones of flow are seen (the placental labyrinth, and the maternal decidua or peripheral region) as shown with highlighting in the bottom left. The placental labyrinth fills first and reaches peak enhancement before the proximal decidua peaks in intensity. FIG. 17 shows the same transient filling sequence when using the liposomal Gd contrast agent. While gadobenate dimeglumine shows a distinct delay between the filling of the placental labyrinth and the maternal decidua, no such delay is noted with the liposomal contrast agent.

Table 2-1 shows the objective impressions of a blinded radiologist who read the images from each contrast agent, at peak intensity, and assessed each placenta for clarity of visualization. The blinded reviewer reviewed all 52 placentae visible in the 14 mice treated with conventional Gd (Multihance) and all 36 placentae visible in the 9 mice treated with liposomal Gd. The $\chi^2$ test yielded a probability of $2\times 10^{-8}$ that the two score distributions were different, suggesting that the two contrast agents enabled images of the same diagnostic quality.

Figure 18:
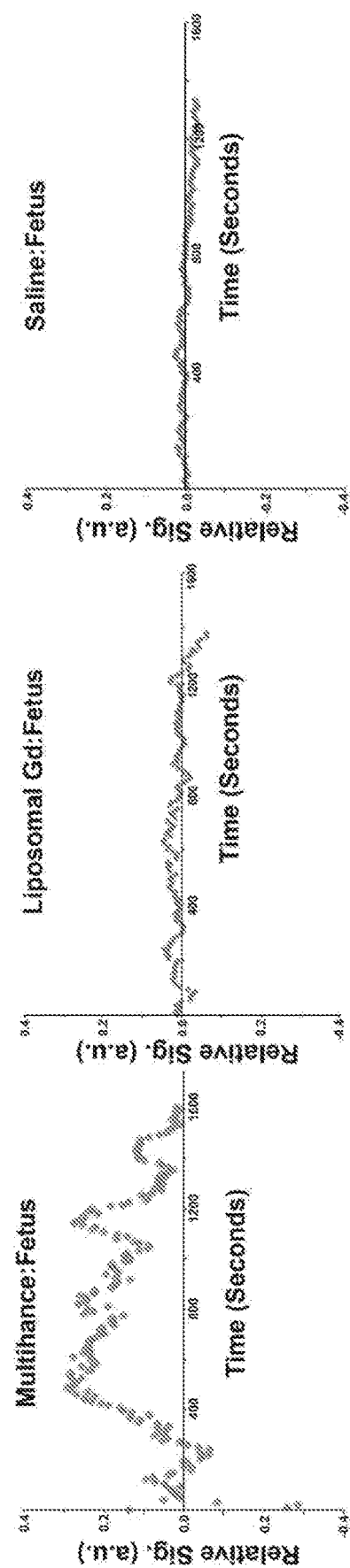
FIG. 18. Typical signal intensity in the fetus, following conventional, liposomal and blank (saline) contrast injections. (a) Multihance® injection shows uptake in the fetal compartment; (b) liposome Gd shows no visible uptake, indistinguishable from the saline blank injection shown in (c).

In every mouse studied, uptake of contrast agent in the fetal compartment was observed with gadobenate dimeglumine whereas with liposomal Gd, no uptake was seen in the fetal compartment even after 72 hr exposure. FIG. 18 shows representative fetal signal following injection of each of the two contrast agents and a control saline injection. The image data was used to calculate absolute Gd concentrations using the methods in Appendix A. Contrast agent concentrations estimated from the MRI data are shown in Table 2-2 using Eqs. A4 and A5.

Figure 19A:
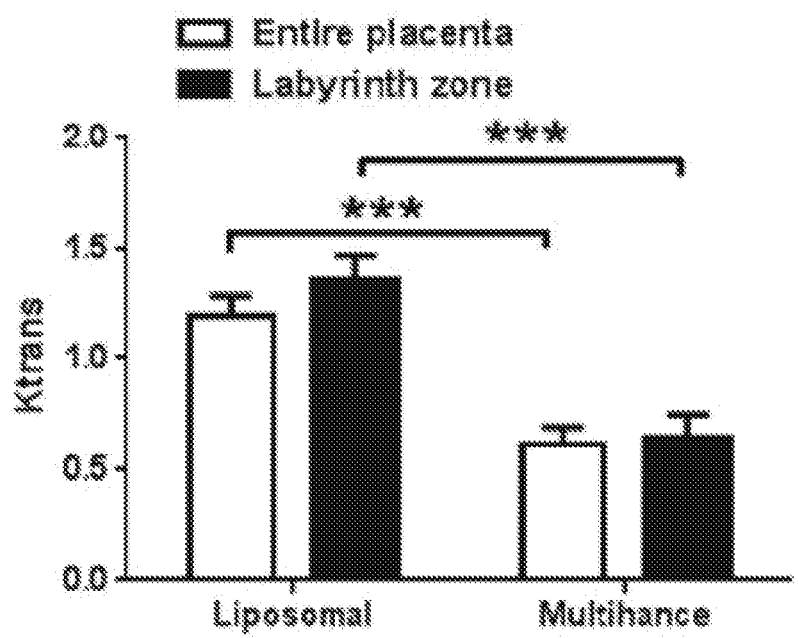
FIGS. 19A-B. Pharmacokinetic (PK) parameters obtained using the RR model. Transfer rates are based on assuming ktrans=0.2 and Kep=0.1 for para-spinal reference tissue. The RR model analysis was performed in two ways: (1) by using signal from the entire placenta as a single compartment (shown in graphs as a white bar) and (2) using only the central labyrinth as an early enhancement signal compartment (black bar). The transfer rates from maternal arteries to placental vascular compartment is Ktrans (shown in A), the efflux rate for placental vascular compartment output is Kep (shown in B). The statistical significance of difference between the measurements two agents is marked using the probability p testing the null hypothesis HO: Compared values are equal. The symbol *** represents p<0.001. For each agent there was no statistically significant difference in PK parameters computed over the entire placenta vs the labyrinth alone. The error bars represent standard error of the mean.
Figure 19B:
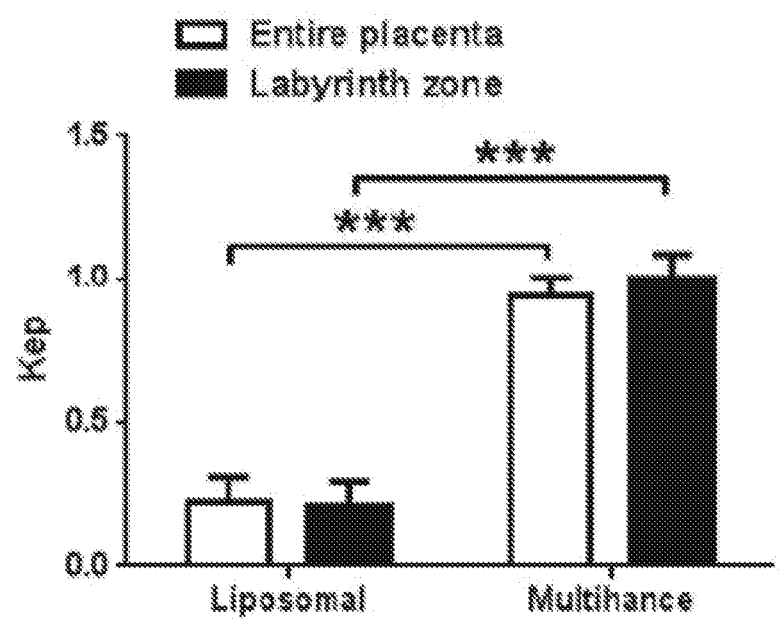

$K^{trans}$ and $K^{ep}$ values for each contrast agent, and considering either the labyrinth zone or the entire placenta as the target tissue, are shown in FIG. 19. The values do not vary significantly with the location of the target ROI within the placenta, but reflect very different values for the two contrast agents.

Figure 20A:
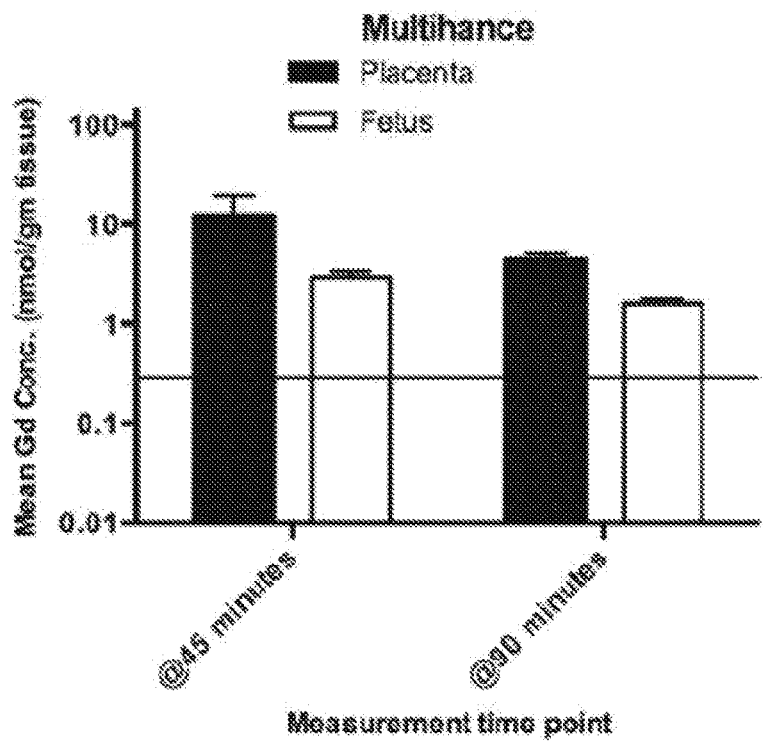
FIGS. 20A-B. Gadolinium assay using ICP-MS, in placentae and fetuses from animals injected with Multihance® (A; n=8) and liposome Gd (B; n=6). Gd concentration is presented at two time-points (45 minutes and 90 minutes post injection for Multihance®, 45 minutes and 72 hours for liposomal Gd). The detection limit is 0.318 nmol/g tissue and is shown by horizontal line. The error bars represent standard error of the mean. Note that the ordinate is plotted on a logarithmic scale, in order to insure visibility of the otherwise very low fetal concentrations following injection of liposomal Gd. Two fetal samples at the 45 minute time point following liposomal Gd injection yielded a Gd measurement above the detection limit, however, it is not possible to rule out the possibility of a small amount of placental tissue contaminating the fetal tissue during excision. All other liposomal Gd samples were below the detection limit. All samples following Multihance® injection were above the detection limit.
Figure 20B:
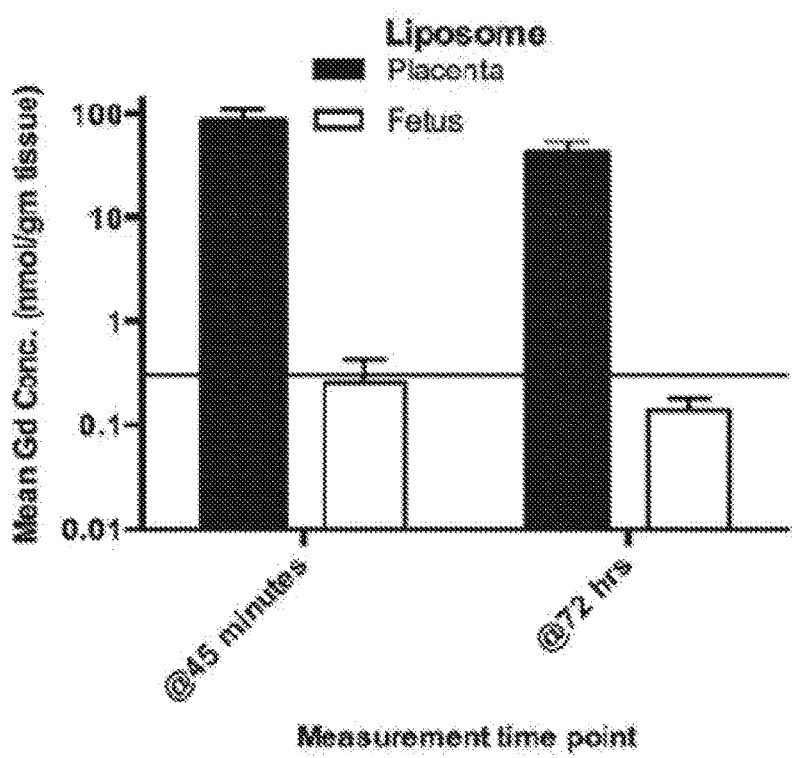

Gadolinium assay by ICP-MS was performed on tissue samples collected at 45 min, 90 min and 72 hrs post-injection. The results of this analysis are shown in FIG. 20. Placental and fetal concentrations were within an order of magnitude of each other at 45 minutes, and within a factor of 2 of each other by 90 minutes when gadobenate dimeglumine was used. When the liposomal agent was used, the fetal concentrations are below the detection limit of the instrument (horizontal line on graph), and at least 2-3 orders of magnitude lower than the placental concentration. The Gd concentration in the fetus resulting from liposomal Gd injection was actually indistinguishable from the negative control (saline treated) control mice at both time points (data not shown).

Discussion:

The short gestational term of the mouse makes the mouse an attractive model for studying placental pathologies throughout the gestational period. The gestational age of mice in this study, at E16.5±1 days, corresponds to the early part of the third trimester in humans. Both the human placenta and the mouse placenta are hemochorionic. There are structural differences, for example the maternal-fetal exchange zone is labyrinthine in mice, while it is villous in humans. However, these structural differences are considered to not affect the overall mechanism of exchange between utero-placental and feto-placental blood.

The placenta is an organ of exchange, and therefore one expects selective, facile transport of species across the placental barrier. Our observation of fetal Gd levels being about 3 orders of magnitude lower than placental levels when liposomal Gd was used, compared to practically equal levels (within an order of magnitude) when conventional Gd chelate was used, (FIG. 20) is consistent with the liposomal particles having a far lower diffusion rate through the maternal-fetal barrier in the placenta. Active transport of liposomes across the placental barrier can be reasonably ruled out, because the PEG coating on the liposomes effectively prevents any specific binding to the surface. In the absence of an active transport mechanism, diffusive or convective processes are the only remaining mechanisms by which molecules or particles can be transported across the placental barrier. There is no convective flow across the barrier of an intact placenta, leaving diffusion as the sole mechanism. The liposomes being 3 orders of magnitude larger than free molecules, it stands to reason they must diffuse far slower, even in bulk medium. In the restricted geometry of the placental barrier, this difference in diffusion rates is likely to be even greater.

Our observation of two zones within each placenta with distinct temporal enhancement patterns is consistent with the early enhancing central labyrinth zone and late enhancing junctional and peripheral zones as previously described by Remus et al. The maternal blood enters the placenta via the penetrating arteries that focus into the central arterial canal (FIG. 15) and flows into the peripheral zone (the labyrinthine sinusoids, which are near the chorionic plate on the fetal side of the placenta). Then, the direction of flow reverses so that it travels away from the chorionic surface and towards the junctional zone. While the two zones do not represent anatomically distinct regions, they can be segmented based on the dynamic signal enhancement pattern. The delivery of blood in this fashion, to the placental labyrinth via the central arterial canal, and its return via the extensive venous circulation, is demonstrated in the DCE-MRI images (FIG. 16 and FIG. 17).

Clear delineation of the placental margin from the uterine wall is a crucial component of the diagnosis of placenta accreta and its related conditions (increta, percreta). Such delineation is a significant challenge today because it is not easy to visualize the thin tissue border that separates the placenta from the maternal uterine wall. Current practice utilizes ultrasound as the first method of visualization, with unclear cases being referred to MRI. No contrast agent is used for MRI in order to eliminate potential exposure of the fetus to Gadolinium. Sensitivity for detection of placental abnormalities using this algorithm is modest, between 80 and 85%. In the absence of contrast, T1 weighted imaging results in poor conspicuity of the placental margin. The benefit of conventional T2-weighted imaging in the absence of exogenous contrast agents is unclear It has been noted that these difficulties with using MRI for the diagnosis of placenta accreta observing that it was not possible to differentiate chorionic villi from decidua basalis. With exogenous contrast however, clear differentiation was observed. Advanced MR techniques such as arterial spin labeling (ASL) and Diffusion Weighted Imaging (DWI) may overcome these limitations using endogenous contrast between tissue and blood. ASL methods provide information on regional flow, without differentiating between the maternal and fetal side of circulation, while DWI provides information on the local diffusion coefficient of protons by measuring intravoxel incoherent motion. However, the Signal to Noise Ratio (SNR) and temporal resolution of both these techniques are significantly worse than contrast enhanced MR. Our observation that liposome Gd agents do not appear to cross in to fetal compartment, suggests a reduced risk to the fetus Their use could enable the visualization of placental boundaries with increased contrast, and the degree of placental invasion could potentially be determined with increased confidence.

SNR in contrast enhanced MRI is a function of both the relaxivity of the contrast agent and the field strength, and increases with both these parameters. The liposomal contrast agent used in this work, however, exhibits dramatically higher relaxivity at low field strength, consistent with the slower rotational correlation time of the liposomal agent compared to the Gd chelate in solution. Thus, while the present work was conducted using a small animal high field 9.4 T magnet, equivalent or superior image quality is anticipated when using clinically relevant 1.5 T field strength.

Beyond simple margin delineation, Dynamic Contrast Enhancement can provide direct information about the net transport of contrast agent in the placenta. Previous work measured trans-placental permeability and placental perfusion using low-molecular conventional contrast agent and a three-compartment model (SAAM II). However, nearby arteries were difficult to visualize in the observed field-of-view and could not provide an accurate vascular input function. We therefore chose the Reference Region (RR) model approach that is not dependent upon a knowledge of arterial or vascular input function.

$K^{trans}$ values in the RR model reflect the filling (perfusion) of the target tissue by the vascular contrast, while the $K^{ep}$ values represent the elimination of contrast. We observe $K^{trans}$ values for the liposomal contrast moderately higher than those for gadobenate dimeglumine, while $K^{ep}$ values for the liposomal contrast are substantially lower than those for gadobenate dimeglumine. The low molecular weight gadobenate dimeglumine diffuses readily past the placental barrier, and therefore reduces the effective amount of contrast in the placenta itself, resulting in the lower $K^{trans}$ value. Similarly, the faster clearance of the low molecular weight chelate by renal filtration results in a higher $K^{ep}$ value compared to that for the liposomal Gd that clears rather slowly due to reticulo-endothelial system uptake and biliary elimination.

Conclusions:

We have demonstrated for the first time that liposomal Gd particles do not penetrate the placental barrier. This could be useful in characterizing placental dysfunction where attachment of placental villi to the myometrium (inner wall of uterus) is difficult to visualize with non-contrast MRI. Perfusion kinetics of the contrast have been established, and in the case of liposomal Gd, are uncorrupted by transport across the placental barrier, and clearance kinetics, thus better reflecting the actual placental perfusion kinetics. Thus, conditions that alter the perfusion could potentially be characterized by this technique. Liposomal Gd chelates could serve as useful agents in the future to study placental architecture and boundary detection in placental anomalies such as accreta. Before use in humans however, both maternal and fetal safety of liposomal Gd will have to to be explicitly established.

Materials and Methods:

Contrast Agents

Multihance® (Bracco Diagnostics Inc. New Jersey, USA) was used as received from the manufacturer. The liposomal Gd agent (NMRX: Nano MR eXtended lifetime) was prepared in-house, following methods described in the literature. Briefly, all lipids (Di Palmitoyl Phosphatidyl Choline (DPPC), Cholesterol, Methoxy Poly Ethylene Glycol-Di Stearoyl Phosphatidyl Ethanolamine (MPEG-DSPE), and Gd-DTPA-bis stearoyl amine (Gd-DTPA-BSA) were dissolved in ethanol in a 30:40:5:25 mole ratio and a final molar concentration (post hydration) of 40 mM and hydrated in a Tris saline buffer containing 500 mg Gd/ml gadobenate dimeglumine, such that the ethanol constituted 10% of total volume, for 1 hour. The self-assembled liposomes were then extruded 7-10 times through 400, 200 and 100 nm Nucleopore track etch membrane in a Lipex 10 ml extruder (Northern Lipids, Vancouver, BC, Canada), the excess ethanol and unencapsulated gadobenate dimeglumine removed by 10 volume exchanges in diafiltration using a 500 kDa cutoff MicroKros module (Spectrum Laboratories, CA). Mean particle size was ~120 nm, measured by dynamic light scattering. Release of Gd from the particles was tested by incubating (at 37° C.) the particle suspension at a 1:5 dilution in phosphate buffered saline (PBS, pH 7.2) and in reconstituted bovine plasma (Sigma-Aldrich, St. Louis, Mo., USA) in a 100 kDa dialysis bag suspended in PBS. The external buffer was sampled at 1, 2, 24, 29, 48, and 52 hours after initiating the incubation, and analyzed for total Gd content by ICP-MS on a Varian 810 ICP-MS system. 3 batches of the nanoparticle contrast agent were tested in this manner, and each time point sampled and analyzed in triplicate.

Animal Models

All animal studies were performed under a protocol approved by the Institutional Animal Welfare Committee of the Baylor College of Medicine. The studies reported in this paper are in accordance with the NC3RS ARRIVE guidelines.

25 female Balb/c mice (7-9 weeks old; average weight 26 grams before pregnancy) were used in this study. Animals were mated with same strain males. The day when a vaginal copulation plug was detected was designated as day 0.5. Pregnant mice were imaged at day 16.5±1. Mice were sacrificed (under the institutional euthanasia protocol) immediately after MRI data collection (except for two mice that received the liposomal Gd agent, and were maintained alive for 72 hours, allowing additional time for possible transport of Gd to the fetus, and then sacrificed). Mice were dissected and the placentae and fetuses removed and transferred individually to 2 ml polycarbonate vials for storage at −81° C. These placentae and fetuses were analyzed using ICP-MS for the direct measurement of Gd concentration.

Animals were anesthetized with 4% Isofluorane/air and transferred supine to the animal-imaging cradle. A 28-gauge catheter was placed in the tail vein. Once transferred to the imaging instrument, isofluorane (2%) was administered continuously via a nose cone. A pressure sensitive pillow was placed on the abdomen and taped in place to monitor respiration. The animal chamber of the imaging probe was maintained at around 30-33° C. The magnet room was maintained at 25-27° C. Heart rate was maintained at steady 50-60 beats-per-minute by adjusting the airflow and isofluorane concentration. MR imaging was performed with Multihance® in 14 mice. Liposomal Gd was used in 9 mice. Two mice were injected with saline as a control for comparison. Contrast agents were diluted to 20 mM and a dose of 0.08 mmol/kg (typically around 100 µL) were prepared for this study. The contrast agent was injected manually by the same operator (3 years of experience with small animals) and at the same rate in each mouse.

DCE-MRI Studies

While the liposomal contrast agent has slow clearance, Multihance® clears rapidly, and timing the image acquisition is critical. We therefore opted to use the DCE-MRI technique to collect a series of images, from which the optimal time point could be selected. DCE-MRI experiments were performed on a horizontal bore 9.4 T Bruker Avance III, 20 cm bore Biospec Spectrometer (Karlsruhe, Germany) with a micro-imaging probe capable of generating gradients of (1000 mT/m). Prior to the in vivo study, the relaxivity of both agents was measured using the variable flip angle technique described in Appendix A. Similarly, the baseline relaxation rates, $T_1(O)$, for placenta and fetus were measured using the same pulse sequence as described in Appendix A.

For the DCE-MRI study, baseline images without contrast enhancement were acquired, followed by a series of images acquired over time during and after the arrival of the contrast agent in the tissue of interest. A 3D-spoiled gradient recalled echo (SPGRE) pulse sequence with a fixed flip angle of 16 degrees was used over 175 measurements. Other parameters are described in Appendix A. The time for a single measurement was 9.25 seconds. Two minutes into the experiment, contrast was injected. Total scan time was 26 minutes and 52 seconds. The acquired signal was used to generate a time-intensity curve and the signal was converted pixel-by-pixel into concentration of the injected agent.

ICP-MS

Wet tissue from placentae or pups was chopped with a scalpel into ~3 mm pieces. A known mass of chopped tissue was then dissolved in 2-4 ml of concentrated nitric acid (14N) and heated at 100° C. till tissue completely dissolved. (Usually, about 30-45 minutes at room temperature and 3 minutes at 100° C. were sufficient). The acid solution was diluted with 10 ml of DI water, causing some precipitation of organic material. The material was centrifuged at 3000 g for 5-10 minutes, and the supernatant used for analysis. Serial dilutions over a $10^6$ range were then made, and spiked with an internal standard of Bi 10 parts per billion (ppb) in 2% nitric acid. ICP-MS analysis was conducted on a Varian 810 ICP-MS system, using the manufacturer's recommended protocol for Gd assay. A spike-recovery study on blank tissue yielded linear response with >90% recovery over a range of 0-900 ppb and >96% response over a range of 0-50 ppb.

Data Analysis:

Image Interpretation:

Due to relatively fast clearance of the Multihance contrast agent from circulation, image intensity peaked about 11-15 seconds after injection. Images from both multihance and liposomal-Gd were compared by a Radiologist to assess its quality and appearance. The images of each placenta in the field of view representing the maximum intensity achieved, were selected for reading. Images collected with the liposomal agent had constant intensity due to the very slow clearance from circulation, so an image from the series was randomly selected. Images were de-identified so the contrast agent used was not revealed, their order randomized, and presented to a blinded reader (pediatric radiologist specializing in maternal-fetal imaging). The reader rated each image on a 5-point scale (0: Placenta not visible, upto 4: clearly visible and margin delineated, comparable to major blood vessel). The scored images were then unblinded and the discrete distribution of scores for images acquired with each contrast agent tabulated. The chi-squared test was used to test the null hypothesis H0: the distributions are not equivalent.

DCE Analysis

MRI data was transferred to an offline workstation and each placental and fetal compartment was segmented as a separate region of interest (ROI) using AMIRA V5.6 software (FEI Visualization Sciences Group, Hillsboro, Oreg.). The segmented regions were transferred to Matlab (Matlab 7.6.0, MathWorks, Natick, Mass., USA) to create a pixel-by-pixel $T_1(0)$ map and $T_1(t)$ map as described in Appendix A. Two placental zones were identified visually from the signal enhancement pattern: the labyrinth zone characterized by early flow enhancement and a peripheral region (maternal decidua) characterized by late flow enhancement that began after the central labyrinth enhancement peaked. The two zones together constitute the entire placenta.

DCE estimates were made for two cases: (1) assuming the placental labyrinth alone as the target tissue, and (2) assuming the entire placenta as the target tissue. A reference region (RR) model was used to estimate transfer rate constants $K^{trans}$ and $K^{ep}$ for the target tissue, (details in Appendix B). For both cases, a reference region in the paraspinal muscle was used, with assumed values of $K^{trans}=0.2$ ml/min/ml tissue and $K^{ep}=0.1$ ml/min/ml.

TABLE 2-1

Placental visibility as rated by a blinded reader (trained maternal-fetal radiologist). The Chi-squared test on the score distributions indicated a probability of $2 \times 10^{-8}$, testing the null hypothesis that the two distributions are different, suggesting that the two contrast agents yielded equivalent images.

| Placenta Visibility | Number observed with Conventional Gd (Multihance) | Number observed with Liposomal Gd (NMRX) |
| --- | --- | --- |
| 1 | 1 | 1 |
| 2 | 6 | 7 |
| 3 | 25 | 17 |
| 4 | 15 | 21 |
| 5 | 7 | 1 |

TABLE 2-2

Placental and fetal concentration of gadolinium peak from MRI data. Mean concentration using estimated $T1_0$ and Eqs. A4 and A5. ROI was placed around the entire placenta and fetal sac.

| Contrast agent | Placental concentration (µmol/L) | Fetal concentration (µmol/L) |
| --- | --- | --- |
| Multihance ® (n = 52) | 0.60 ± 0.51 | 0.027 ± 0.01 |
| Liposome Gd (n = 26) | 1.12 ± 0.92 | Not Detectable |
| Control (Saline only) | Not Detectable | Not Detectable |

Example 3

Morbidly Adherent Placenta (MAP) is a devastating condition characterized by invasion of the placenta into the uterine wall. MAP incidence has increased nearly 10-fold in the last 30 years. While this increase has largely coincided with the increase in C-sections, in one multi-center population-based study, over half of the cases were in nulliparous women, or those with no history of C-section, suggesting that spontaneous MAP (in the absence of known risk factors) is a significant occurrence. Diagnosis of MAP remains challenging, even with ultrasound followed by MRI in indeterminate cases: only about half of the cases of MAP are suspected prior to childbirth. MAP results in massive blood loss (25% of cases), hysterectomy (70% of cases) and ICU admission (30% of cases), at rates far higher than in the non-MAP population.

While ultrasound is the first line imaging modality for the detection of MAP, sensitivity and specificity are imperfect with considerable variation in interobserver reliability therefore, there is increasing use of MRI, usually in the $2^{nd}$ and $3^{rd}$ trimester. Gadolinium (Gd) contrast agents enhance the diagnostic accuracy of MRI for MAP. However, concerns over fetal exposure to Gd have eliminated its use in the U.S., while in the rest of the world, it is used cautiously. Yet, Gd agents have a remarkably low adverse event rate of 0.1-0.3%. A recent prospective study compiled data over an 8 year period and over 130,000 administrations of Gd contrast in humans (both genders, all ages, and including pregnant females), with no specification on the indication. The study also included both academic and community hospitals. Adverse events in this study were specified as "any reported objective or subjective sign", whether clinically relevant or not. Even with this extremely broad criterion, the reported AE rate was vanishingly small: 0.18%. Less than 0.01% were classified as "serious", the rest were considered "mild." The vast majority were some form of allergic reaction, and were easily treated with diphenhydramine or in a small handful of cases, using steroids.

In pregnant females, safety considerations apply to both the mother and the fetus. While there have been no prospective studies of Gd safety in pregnant women, there have been a number of retrospective studies, and several animal studies. In rodents and in non-human primates, there was no discernible effect of Gd exposure in the mothers or the offspring. In humans, retrospective analysis of clinical data shows no adverse effects on the mother, and no effect on infants when the Gd exposure took place during the first trimester. However, when Gd exposure took place in the $2^{nd}$ or $3^{rd}$ trimester, there was an association with increased risk of rheumatologic or inflammatory conditions in the offspring. Fraum et al., JMRI 2017. Another study (Ray et al., JAMA 316:952-61 (2016)). focused on the first trimester and showed an increased risk of rheumatological or inflammatory conditions even from Gd exposure in this period. Thus, eliminating fetal exposure is one way of improving the safety of Gd agents in pregnancy. Unlike conventional Gd chelates that appear to readily diffuse across the placental barrier, this Example demonstrates that embodiments of the liposomal Gd contrast agents disclosed herein are shown to not do so.

Methods

Fluorescent liposomes for perfused placenta study: For the perfusion of both the maternal and fetal compartments of experimental placenta, Krebs solution (Sigma-Aldrich, St. Louis, Mo.) was used. The solution contained D-glucose (2.07 g/L), NaCl (6.95 g/L), KCl (0.35 g/L), $MgSO_4$ (0.144 g/L), $KH_2PO_4$ (0.163 g/L), $NaHCO_3$ (2.1 g/L), EDTA (9.7 mg/L), $CaCl_2.2H_2O$ (0.37 g/L), 2,000-U/l heparin (S agent Pharmaceuticals; Schaumburg, Ill.) and 50-mg/1 gentamicin (Sigma-Aldrich; St. Louis, Mo.). A 40,000 molecular-weight dextran (Spectrum Chemical; New Brunswick, N.J.) was dissolved in the fetal and maternal solutions at concentrations of 30 g/L and 7.5 g/L, respectively, to maintain a proper colloid-osmotic balance in the perfused placental tissue. These buffers were used for the perfusion of the maternal and fetal sides of placenta during the entire course of the experiment. The fetal perfusion solution was equilibrated with a 95 percent $N_2$/5 percent $CO_2$ gas mixture throughout the experiment, while the maternal solution was equilibrated with a 95% $O_2$/5% $CO_2$. As a surrogate for the liposomal contrast agent, rhodamine bearing liposomes were used (Bhavane et al., *Circ. Cardiovasc. Imaging* Jan. 24, 2013). Liposomes were prepared using 1,2-dipalmitoyl-sn-glycero-3-phosphatidylcholine (DPPC), cholesterol, N-(carbony-methoxy polyethyleneglycol 2000)-1,2-distearoyl-sn-glycero-3 phosphoethanolamine (mPEG-DSPE), and Lissamine rhodamine B 1,2-dihexadecanoyl-sn-glycero-3-phosphoethanolamine triethylammonium salt (Rhodamine-DHPE) (Invitrogen Corp., Carlsbad, Calif.) in the molar ratio DPPC:CHOL:mPEG-DSPE:Rhodamine-DHPE=61.9:35:3:0.1.

Cotyledon selection and cannulation: Women with pregnancies classified as Normal, or exhibiting Gestational Diabetes Mellitus (GDM), or Intra Uterine Growth Restriction (IUGR) were chosen for this study. Prior to delivery, all patients signed a consent form approved by the Institutional Review Board. The procedure closely followed a previously published protocol. Bednov et al. *Placenta* Aug. 31, 2015. Placental tissues were obtained from women delivering at term after Cesarean sections. Three placentae from each of the conditions (Normal, GDM, IUGR) were used in this study. Immediately after delivery, placenta was transported to a dedicated placental perfusion room located in the labor and delivery suite where it was further processed. Each placental sample was weighed and placed in a tray filled with normal saline solution at room temperature. The chorionic and amniotic membranes were removed. A cotyledon from the periphery of the placenta with no evidence of hematoma, infarct, recent hemorrhage or tissue disruption and containing a single pair of arterial and venous vessels was then selected for cannulation.

The "artery-vein" pair of a chorionic plate was cannulated. A few milliliters of buffer solution containing heparin were injected into the cannulated artery immediately after cannulation to distend partially collapsed vessel branches and for anticoagulation. Proper cannulation was confirmed by back flow from the cannulated vein following injection of buffer into its corresponding artery.

Placenta perfusion: Both the cannulated artery and vein of placenta were connected to a digital peristaltic pump (Welch Vacuum, model 3200C, Welch; Niles, Ill.) with initial flow rate of 1.5 ml/min. The cannulated cotyledon was then mounted onto the spikes of a metal compression ring and clamped to an acrylic cylinder with butterfly nuts. The excess of surrounding placental tissue was removed. The mounted assembly was then placed (with the maternal surface facing up) into a double-walled thermostabilizing perfusion chamber (Specialty Glass, Inc., Houston, Tex.) filled with saline. The temperature in both the fetal and maternal circulation systems, as well as in the water-warming perfusion chamber, was set to 37° C.

Placental leakage between maternal and fetal compartments was checked by measuring collected volumes of fetal perfusion solution over a 30-minute period. Leakage of less than 10%/hour was considered acceptable. Maternal perfusion was then established by inserting four evenly distributed metal cannulae into the maternal surface through the basal plate into the placental intervillous space 2-4 mm below the decidual surface. The perfusate left the intervillous space through several venous openings in the decidual plate and was continuously drained by a back-flow pump system.

Normoxic conditions in the perfused cotyledon were established by ventilation of the maternal perfusion solution with 95% $O_2$/5% $CO_2$ gas mixture and the fetal perfusion buffer with 95% $N_2$/5% $CO_2$.

The liposomal contrast agent was then injected into the maternal circulation side of the perfused organ. Samples of both maternal and fetal recirculating fluids were collected, at time points: 1, 2, 4, 8, 12, 16, 32, 40, 60 minutes. Rhodamine content of the samples was assayed in triplicate, using fluorescence (Ex/Em: 540 nm/625 nm) spectroscopy. Samples collected from 12 to 60 minutes (after the startup transients had equilibrated) were used to estimate the total lipid content in each sample. The mean lipid concentration on each side of the placental barrier, post-injection, relative to the value pre-injection was used as an indicator of the permeability of the liposomes through the placental barrier.

Results:

Liposome-lipid concentrations in the maternal circuit averaged around 300-500 μM, consistent with the concentration introduced into the circuit. Concentrations in the fetal circuit were 500-1000 fold lower. Notably, abnormalities in pregnancy (gestational diabetes, and fetal growth restriction) did not appear to affect the placental permeability of the liposome agent, both maternal and fetal concentrations of the agent were indistinguishable from the corresponding levels in normal placentae.

The fact that polyethylene glycol coated liposomes have long circulating properties, and can function as blood pool agents forms the basis for clinically used liposomal doxorubicin, and several imaging agents that have been tested in numerous animal models. Of relevance to the potential use in placental imaging however, is the possibility that these agents could penetrate the human placental barrier, particularly in late pregnancy when fetal Gd exposure has been correlated with an increased risk of rheumatological and immunological conditions. In term placentae representative of normal, GDM and growth-restricted pregnancy, however, the experiments performed by the inventors show that these liposomal particles do not penetrate the placental barrier. As measured by a fluorescent tracer (lipid-rhodamine) that remains associated with the lipid bilayer of the liposome, concentrations of liposomes in the fetal circuit of perfused placentae were 3 orders of magnitude lower than the concentrations in the maternal circuit, consistent with the levels measured in the rat fetuses and maternal blood.

REFERENCES

Avdonin P V, Buhler F R, Tkachuk V A (2000) Ca2+-agonistic effect of a T-type Ca-channel blocker mibefradil (Ro 40-5967). Membr Cell Biol 13:645-655.

Bhavane R, Badea C, Ghaghada K B, Clark D, Vela D, Moturu A, et al. Dual-Energy Computed Tomography Imaging of Atherosclerotic Plaques in a Mouse Model Using a Liposomal-Iodine Nanoparticle Contrast Agent. Circ Cardiovasc Imaging. Jan. 24, 2013.

Caviedes B E, Herranz J L (2001) [Use of antiepileptic drugs in non epileptic disorders]. Rev Neurol 33:241-249.

Chaplan S R, Bach F W, Pogrel J W, Chung J M, Yaksh T L (1994) Quantitative assessment of tactile allodynia in the rat paw. Journal of neuroscience methods 53:55-63.

Chaudhry V, Rowinsky E K, Sartorius S E, Donehower R C, Cornblath D R (1994) Peripheral neuropathy from taxol and cisplatin combination chemotherapy: clinical and electrophysiological studies. Annals of neurology 35:304-311.

Cribbs L L, Gomora J C, Daud A N, Lee J H, Perez-Reyes E (2000) Molecular cloning and functional expression of Ca(v)3.1c, a T-type calcium channel from human brain. FEBS Lett 466:54-58.

Decosterd I, Woolf C J (2000) Spared nerve injury: an animal model of persistent peripheral neuropathic pain. Pain 87:149-158.

Fraum T J, Ludwig D R, Bashir M R, Fowler K J. Gadolinium-based contrast agents: A comprehensive risk assessment. Journal of magnetic resonance imaging Jan. 13, 2017.

Gomora J C, Daud A N, Weiergraber M, Perez-Reyes E (2001) Block of cloned human T-type calcium channels by succinimide antiepileptic drugs. Mol Pharmacol 60:1121-1132.

Huguenard J R (1998) Low-voltage-activated (T-type) calcium-channel genes identified. Trends Neurosci 21:451-452.

Huguenard J R (2002) Block of T -Type Ca(2+) Channels Is an Important Action of Succinimide Antiabsence Drugs. Epilepsy Curr 2:49-52.

Jagodic M M, Pathirathna S, Joksovic P M, Lee W, Nelson M T, Naik A K, Su P, Jevtovic-Todorovic V, Todorovic S M (2008) Upregulation of the T-type calcium current in small rat sensory neurons after chronic constrictive injury of the sciatic nerve. J Neurophysiol 99:3151-3156.

Jagodic M M, Pathirathna S, Nelson M T, Mancuso S, Joksovic P M, Rosenberg E R, Bayliss D A, Jevtovic-Todorovic V, Todorovic S M (2007) Cell-specific alterations of T-type calcium current in painful diabetic neuropathy enhance excitability of sensory neurons. J Neurosci 27:3305-3316.

Jarvis M F, Scott V E, McGaraughty S, Chu K L, Xu J, Niforatos W, Milicic I, Joshi S, Zhang Q, Xia Z (2014) A peripherally acting, selective T-type calcium channel blocker, ABT-639, effectively reduces nociceptive and neuropathic pain in rats. Biochemical pharmacology 89:536-544.

Jenkins I D, Lacrampe F, Ripper J, Alcaraz L, Le P V, Nikolakopoulos G, de Almeida Leone P, White R H, Quinn R J (2009) Synthesis of four novel natural product inspired scaffolds for drug discovery. The Journal of organic chemistry 74:1304-1313.

Kraus R L, Li Y, Gregan Y, Gotter A L, Uebele V N, Fox S V, Doran S M, Barrow J C, Yang Z Q, Reger T S, Koblan K S, Renger J J (2010) In vitro characterization of T-type calcium channel antagonist TTA-A2 and in vivo effects on arousal in mice. J Pharmacol Exp Ther 335:409-417.

Latham J R, Pathirathna S, Jagodic M M, Choe W J, Levin M E, Nelson M T, Lee W Y, Krishnan K, Covey D F, Todorovic S M, Jevtovic-Todorovic V (2009) Selective T-type calcium channel blockade alleviates hyperalgesia in ob/ob mice. Diabetes 58:2656-2665.

Lee M (2014) Z944: a first in class T-type calcium channel modulator for the treatment of pain. Journal of the peripheral nervous system: JPNS 19 Suppl 2:S11-12.

Messinger R B, Naik A K, Jagodic M M, Nelson M T, Lee W Y, Choe W J, Orestes P, Latham J R, Todorovic S M, Jevtovic-Todorovic V (2009) In vivo silencing of the Ca(V)3.2 T-type calcium channels in sensory neurons alleviates hyperalgesia in rats with streptozocin-induced diabetic neuropathy. Pain 145:184-195.

Nelson S C, Friedman H S, Oakes W J, Halperin E C, Tien R, Fuller G N, Hockenberger B, Scroggs M W, Moncino M, Kurtzberg J, et al. (1992) Successful therapy for trilateral retinoblastoma. Am J Ophthalmol 114:23-29.

Perez-Reyes E (2003) Molecular physiology of low-voltage-activated t-type calcium channels. Physiol Rev 83:117-161.

Perez-Reyes E (2010) G protein-mediated inhibition of Cav3.2 T-type channels revisited. Molecular pharmacology 77:136-138.

Perez-Reyes E, Van Deusen A L, Vitko I (2009) Molecular Pharmacology of Human Cav3.2 T-Type Ca2+ Channels: Block by Antihypertensives, Antiarrhythmics, and Their Analogs. Journal of Pharmacology and Experimental Therapeutics 328:621-627.

Pexton T, Moeller-Bertram T, Schilling J M, Wallace M S (2011) Targeting voltage-gated calcium channels for the treatment of neuropathic pain: a review of drug development. Expert opinion on investigational drugs 20:1277-1284.

Talley E M, Cribbs L L, Lee J H, Daud A, Perez-Reyes E, Bayliss D A (1999) Differential distribution of three members of a gene family encoding low voltage-activated (T-type) calcium channels. J Neurosci 19:1895-1911.

Todorovic S M, Jevtovic-Todorovic V (2011) T-type voltage-gated calcium channels as targets for the development of novel pain therapies. British journal of pharmacology 163:484-495.

Tringham E, Powell K L, Cain S M, Kuplast K, Mezeyova J, Weerapura M, Eduljee C, Jiang X, Smith P, Morrison J L, Jones N C, Braine E, Rind G, Fee-Maki M, Parker D, Pajouhesh H, Parmar M, O'Brien T J, Snutch T P (2012) T-type calcium channel blockers that attenuate thalamic burst firing and suppress absence seizures. Science translational medicine 4:121ra119.

Uebele V N, Gotter A L, Nuss C E, Kraus R L, Doran S M, Garson S L, Reiss D R, Li Y, Barrow J C, Reger T S, Yang Z Q, Ballard J E, Tang C, Metzger J M, Wang S P, Koblan K S, Renger J J (2009) Antagonism of T-type calcium channels inhibits high-fat diet-induced weight gain in mice. J Clin Invest 119:1659-1667.

Wang Y, Liu J J, Dransfield P J, Zhu L, Wang Z, Du X, Jiao X, Su Y, Li A R, Brown S P, Kasparian A, Vimolratana M, Yu M, Pattaropong V, Houze J B, Swaminath G, Tran T, Nguyen K, Guo Q, Zhang J, Zhuang R, Li F, Miao L, Bartberger M D, Correll T L, Chow D, Wong S, Luo J, Lin D C, Medina J C (2013) Discovery and Optimization of Potent GPR40 Full Agonists Containing Tricyclic Spirocycles. ACS medicinal chemistry letters 4:551-555.

Xiang Z, Thompson A D, Brogan J T, Schulte M L, Melancon B J, Mi D, Lewis L M, Zou B, Yang L, Morrison R, Santomango T, Byers F, Brewer K, Aldrich J S, Yu H, Dawson E S, Li M, McManus O, Jones C K, Daniels J S, Hopkins C R, Xie X S, Conn P J, Weaver C D, Lindsley C W (2011) The Discovery and Characterization of ML218: A Novel, Centrally Active T-Type Calcium Channel Inhibitor with Robust Effects in STN Neurons and in a Rodent Model of Parkinson's Disease. ACS chemical neuroscience 2:730-742.

Xie X, Brogan J T, Schulte M L, Mi D, Yu H, Dawson E S, Li M, McManus O, Engers J, Lewis L M, Thompson A, Jones C K, Weaver C D, Lindsley C W (2010) Scaffold Hopping Affords a Highly Selective in vitro and in vivo T-Type Calcium Inhibitor Probe Free From IP Issues. In: Probe Reports from the NIH Molecular Libraries Program Bethesda (Md.).

Xie X, Lancaster B, Peakman T, Garthwaite J (1995) Interaction of the antiepileptic drug lamotrigine with recombinant rat brain type IIA Na+ channels and with native Na+ channels in rat hippocampal neurones. Pflugers Archiv: European journal of physiology 430:437-446.

Xie X, Van Deusen A L, Vitko I, Babu D A, Davies L A, Huynh N, Cheng H, Yang N, Barrett P Q, Perez-Reyes E (2007) Validation of high throughput screening assays against three subtypes of Ca(v)3 T-type channels using molecular and pharmacologic approaches. Assay and drug development technologies 5:191-203.

Yang Z Q, Barrow J C, Shipe W D, Schlegel K A, Shu Y, Yang F V, Lindsley C W, Rittle K E, Bock M G, Hartman G D, Uebele V N, Nuss C E, Fox S V, Kraus R L, Doran S M, Connolly $T_M$, Tang C, Ballard J E, Kuo Y, Adarayan E D, Prueksaritanont T, Zrada M M, Marino M J, Graufelds V K, DiLella A G, Reynolds L I, Vargas H M, Bunting P B, Woltmann R F, Magee M M, Koblan K S, Renger J J (2008) Discovery of 1,4-substituted piperidines as potent and selective inhibitors of T-type calcium channels. J Med Chem 51:6471-6477.

Yue J, Liu L, Liu Z, Shu B, Zhang Y (2013) Upregulation of T-type Ca2+ channels in primary sensory neurons in spinal nerve injury. Spine 38:463-470.

Zhang Y F, Gibbs J W, 3rd, Coulter D A (1996) Anticonvulsant drug effects on spontaneous thalamocortical rhythms in vitro: ethosuximide, trimethadione, and dimethadione. Epilepsy Res 23:15-36.

What is claimed is:

1. A compound according to Formula I:

$$R^1\text{-}L^1\text{-}X^1\text{---}(CH_2CH_2O(CH_2CH_2O)\text{---}CH_2CH_2)\text{---}X^2\text{-}L^2\text{-}R^2 \quad (I)$$

wherein
- $R^1$ is a phospholipid;
- $L^1$ is a linker selected from a bond, substituted or unsubstituted alkyl, and substituted or unsubstituted heteroalkyl;
- $X^1$ and $X^2$ are independently selected from O and NH;
- n is an integer from 5 to 500; and
- $R^2$ is a paramagnetic metal ion chelate comprising a macrocyclic ligand complexing a paramagnetic metal ion, said chelate having a thermodynamic stability constant (log $K_{GdL}$) of at least about 20; and wherein $L^2$ is:

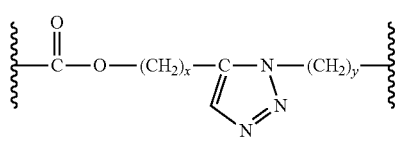

wherein x and y are independently selected from the integers 0, 1, and 2.

2. The compound according to claim 1, wherein said macrocyclic ligand is a tetraaza macrocycle.

3. The compound according to claim 1, wherein said macrocyclic ligand has a formula selected from:

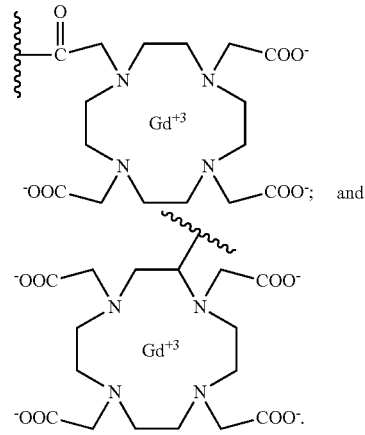

4. The compound according to claim 1, wherein said phospholipid is:

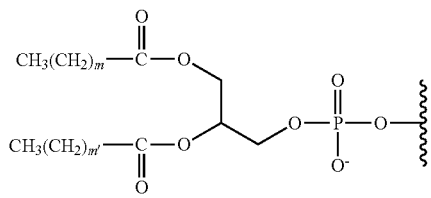

wherein
m and m' are independently selected integers from 4 to 24.

5. The compound according to claim 4, wherein m=m' and is a member selected from the integers from 10, 11, 12, 13, 14, 15, 16, 17, 18, 19, 20, 21 and 22.

6. The compound according to claim 1, wherein $L^1$ is:

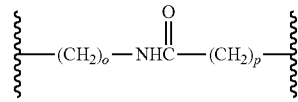

wherein
o and p are independently selected from the integers 0, 1 and 2.

7. The compound according to claim 4, wherein $R^1$-$L^1$ is:

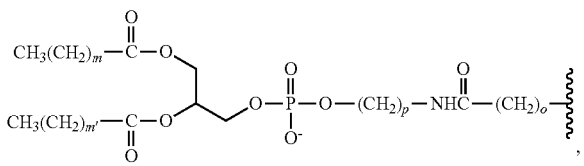

, wherein o and p are independently selected from the integers 0, 1, and 2.

8. The compound according to claim 6, wherein $L^2$-$R^2$ is:

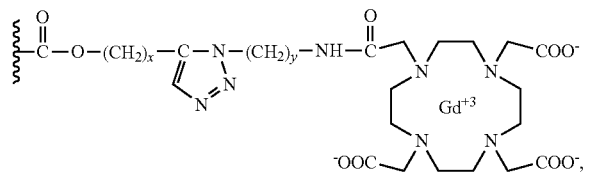

wherein x and y are independently selected from the integers 0, 1, and 2.

9. A liposome comprising a compound according to claim 1 as a first lipid component of the liposome membrane.

10. The liposome according to claim 9, further comprising a second liposome component of the liposome membrane, wherein said second component is a member selected from distearoyl phosphatidylcholine (DSPC), 1,2-dipalmitoyl-sn-glycero-3-phosphocholine (DPPC), hydrogenated soy phosphatidylcholine (HSPC), cholesterol, 1,2-distearoyl-sn-glycero-3-phosphoethanolamine-mPEG (DSPE-mPEG) and a combination thereof.

11. The liposome according to claim 10, wherein said liposome comprises:
  (i) about 1% to about 15% of a lipid according to claim 1;
  (ii) about 50% to about 60% matrix lipid selected from distearoyl phosphatidylcholine (DSPC), 1,2-dipalmitoyl-sn-glycero-3-phosphocholine (DPPC), hydrogenated soy phosphatidylcholine (HSPC) and a combination thereof;
  (iii) about 10% to about 40% cholesterol; and
  (iv) about 1% to about 5% 2-distearoyl-sn-glycero-3-phosphoethanolamine-mPEG (DSPE-mPEG).

12. The liposome according to claim 9, wherein said paramagnetic chelate has a T1 relaxivity at about 1 to about 3 Tesla, which is at least about 4- to about 8-times greater than the same paramagnetic chelate not incorporated into said liposome.

13. A pharmaceutical formulation comprising the liposome according to claim 9, and a pharmaceutically acceptable carrier in which said liposome is suspended, wherein said formulation is a unit dosage format formulation comprising an amount of said liposome sufficient to perform a contrast enhanced magnetic resonance imaging study on an adult patient weighing about 70 kg.

14. A method of acquiring a contrast enhanced magnetic resonance image of a pregnant female subject, said method comprising:
  (a) administering to said subject a liposome, wherein the membrane of the liposome comprises a compound according to claim 1; and
  (b) acquiring said magnetic resonance image of said subject, wherein the retroplacental space is visible in the magnetic resonance image of said subject.

15. The method according to claim 14, wherein the macrocyclic ligand is 1,4,7,10-tetraazacyclododecane-1,4,7,10-tetraacetic acid.

16. The method according to claim 14, wherein the paramagnetic metal ion is $Gd^{+3}$.

17. The method according to claim 14, wherein the liposome encapsulates a contrast agent comprising gadobenate dimeglumine, gadopentate dimeglumine, or gadofosveset trisodium.

18. The method according to claim 14, wherein the liposome has a diameter in the range of 100 to 150 nm and a molecular weight in the range of $1.8 \times 10^5$ to $2.2 \times 10^5$ kD.

19. The method according to claim 14, wherein the liposome is comprised in a pharmaceutical composition, and wherein less than about 5% of the liposome in the pharmaceutical composition crosses the placenta and is delivered to the circulatory system of the fetus.

* * * * *

UNITED STATES PATENT AND TRADEMARK OFFICE
CERTIFICATE OF CORRECTION

PATENT NO. : 11,052,162 B2
APPLICATION NO. : 16/333832
DATED : July 6, 2021
INVENTOR(S) : Ananth Annapragada et al.

Page 1 of 1

It is certified that error appears in the above-identified patent and that said Letters Patent is hereby corrected as shown below:

In the Claims

Claim 1, Column 41, Line 45:
Delete "$R^1$-$L^1$-$X^1$—($CH_2CH_2O(CH_2CH_2O)$—$CH_2CH_2$)—$X^2$-$L^2$-$R^2$" and replace with
-- $R^1$—$L^1$—$X^1$—($CH_2CH_2O(CH_2CH_2O)_nCH_2CH_2$)—$X^2$—$L^2$—$R^2$ --.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*